United States Patent [19]

Desreux et al.

[11] Patent Number: 6,056,939
[45] Date of Patent: May 2, 2000

[54] SELF-ASSEMBLING HETEROPOLYMETALLIC CHELATES AS IMAGING AGENTS AND RADIOPHARMACEUTICALS

[76] Inventors: Jean F. Desreux, 11 Allée des Rouges-gorges, B-4031, Angleur; Vincent Jacques, 46/1 Rue Principale, B-4347, Fexhe-Le-Haut-Clocher; Valérie Humblet, 8 Clos des Mesanges, B-4300, Waremme; Martine Hermann, 68 Rue abbé Toussaint, B-4980 Ovifat; Vinciane Comblin-Tholet, 78 Rue des Hineux, B-4040 Herstal, all of Belgium; Michael F. Tweedle, 72 Library Pl., Princeton, N.J. 08540

[21] Appl. No.: 09/141,710

[22] Filed: Aug. 28, 1998

[51] Int. Cl.$^7$ ............... A61K 51/00; A61M 36/14
[52] U.S. Cl. ............... 424/1.65; 534/14; 424/1.11
[58] Field of Search ............... 424/1.11, 1.65, 424/9.1, 9.3, 9.4, 9.5, 9.6, 9.7, 9.8; 562/607; 534/7, 10–16; 206/223, 569, 570; 540/121; 544/1; 546/1, 51, 152, 184, 249

[56] References Cited

U.S. PATENT DOCUMENTS

| | | | |
|---|---|---|---|
| 4,885,363 | 12/1989 | Tweedle et al. | 540/2 |
| 5,250,672 | 10/1993 | Sadler et al. | 536/7.3 |
| 5,284,647 | 2/1994 | Niedbala et al. | 424/81 |
| 5,358,704 | 10/1994 | Desreux et al. | 424/9 |

FOREIGN PATENT DOCUMENTS

| WO 92/172215 | 3/1992 | WIPO . |
|---|---|---|
| WO 95/31219 | 5/1995 | WIPO . |

OTHER PUBLICATIONS

Spectrochim, Acta 49A, 1315–1322, 1993 (Aime et al).
Angew. Chem. Int. Ed. Engl. 30, 1139–1141, 1991 (Blake et al).
Inorg. Chem., 31:741–746, 1992 (Benelli et al).
J. Chem. Soc., Dalton, Trans., 409–412, 1993 (Benelli et al).
J. Magn. Reson. Imaging, 7, 472–477, 1997 (Dupas et al).
J. Nucl. Med., 38, 1180–1185, 1997 (DeNardo et al).
Bioconjugate Chem., 9, 87–93, 1998 (Williams et al).
Inorg. Chem., 37, 577–589, 1998 (Martin et al).
Helv. Chim. Acta, 78, 1651–1672, 1995 (Piguet et al).
Chem. Rev., 93, 1137–1156, 1993 Jurisson et al.
Pure Appl. Chem, 65, 515–520, 1993 (Kumar et al).

*Primary Examiner*—Jose' G. Dees
*Assistant Examiner*—Dameron Jones
*Attorney, Agent, or Firm*—Imre Balogh

[57] ABSTRACT

Metal complexes of new ligands of the formula

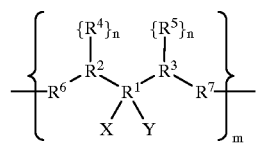

are useful as agents for medical imaging, particularly MRI, for in vitro or in vivo diagnostic or as radiopharmaceuticals. In these compounds, X—$R^1$—Y is a coordinating group able to form a highly stable complex with metal ions. Suitable units are for example derivatives of ortho-phenanthroline or of an hydroxamic acid. $R^2$ and $R^3$ are reactive functions such as amines or carboxylic groups. $R^4$ and $R^5$ are ligands, for instance diethylenetriaminepentaacetic acid 1,4,7,10-tetraacetic acid (DTPA), 1,4,7,10-tetraazacyclododecane-1,4,7,10-tetraacetic acid (DOTA) or 1,4,8,11-tetraazacyclotetradecane-N, N', N", N'"-tetraacetic acid (TETA), of a different type than the X—$R^1$—Y units and able to strongly encapsulate metal ions with which the X—$R^1$—Y moieties form less stable chelates. Stable high molecular weight multimetallic entities are spontaneously formed by these ligands that spontaneously associate around metal ions through the X—$R^1$—Y units. Higher relaxivities thus are achieved. Mixed-complexes containing two different radionuclides are also obtained thus allowing imaging and therapy with one single chelate.

33 Claims, 8 Drawing Sheets

FIG. I.A
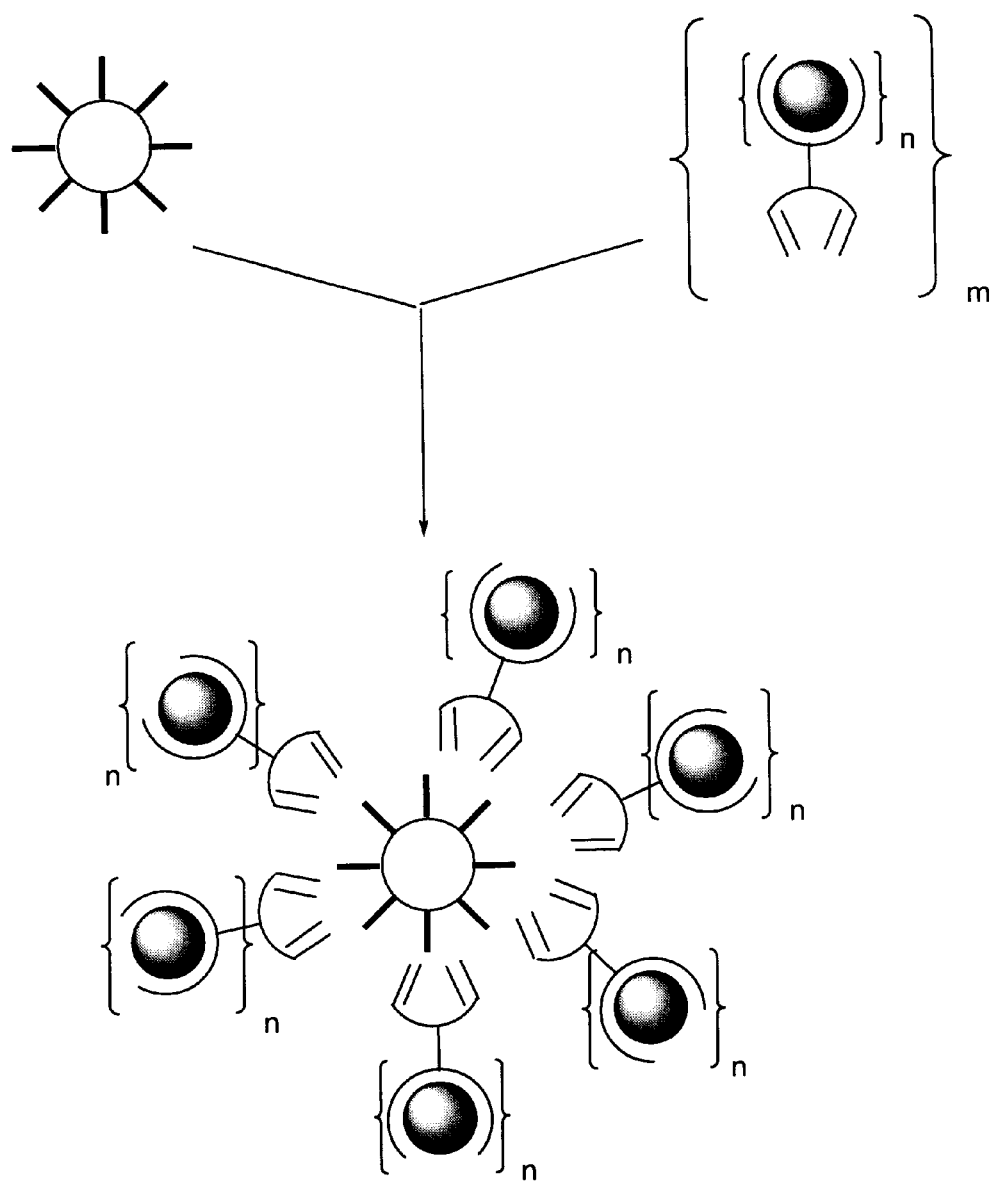

FIG. I.B
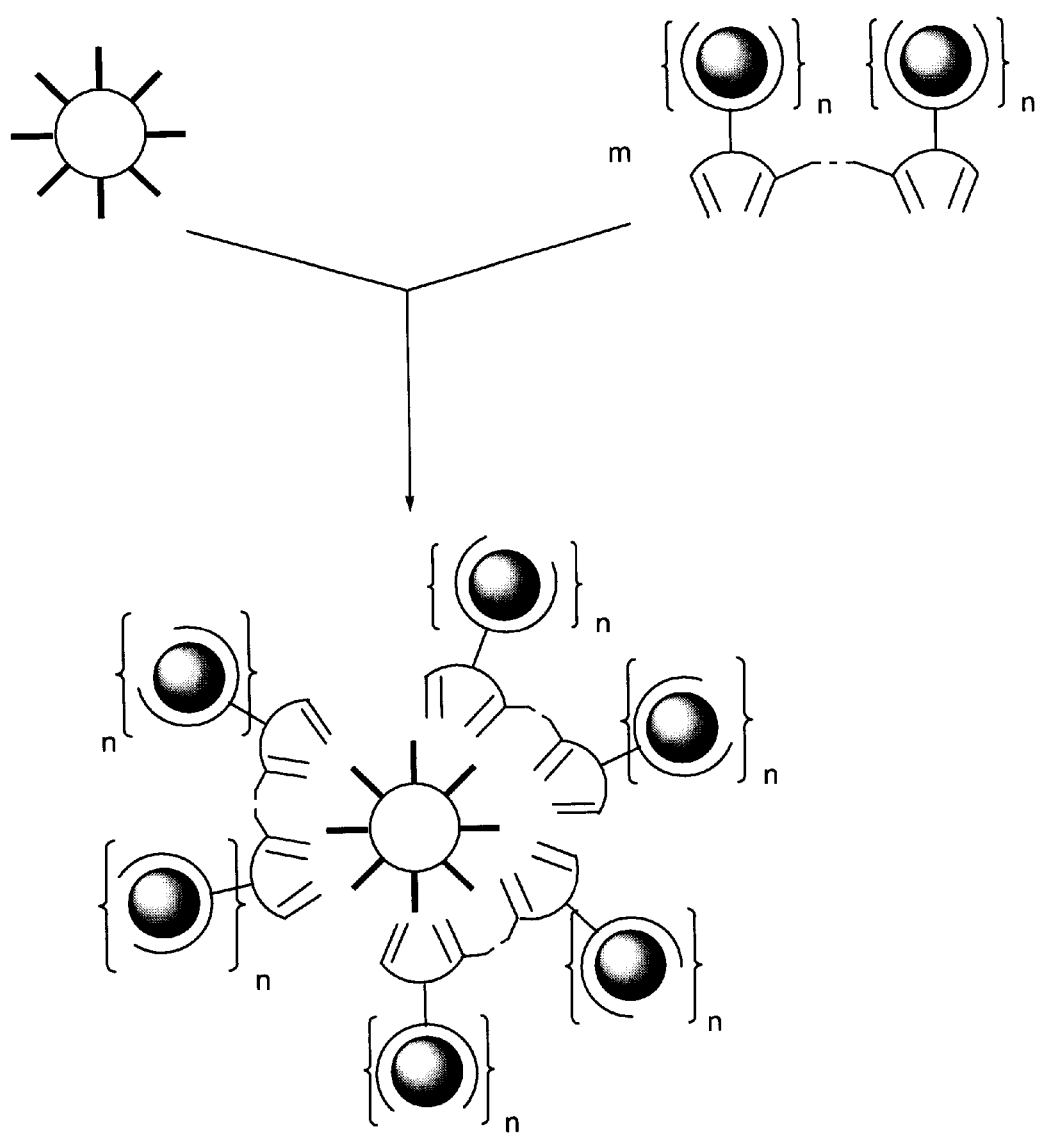

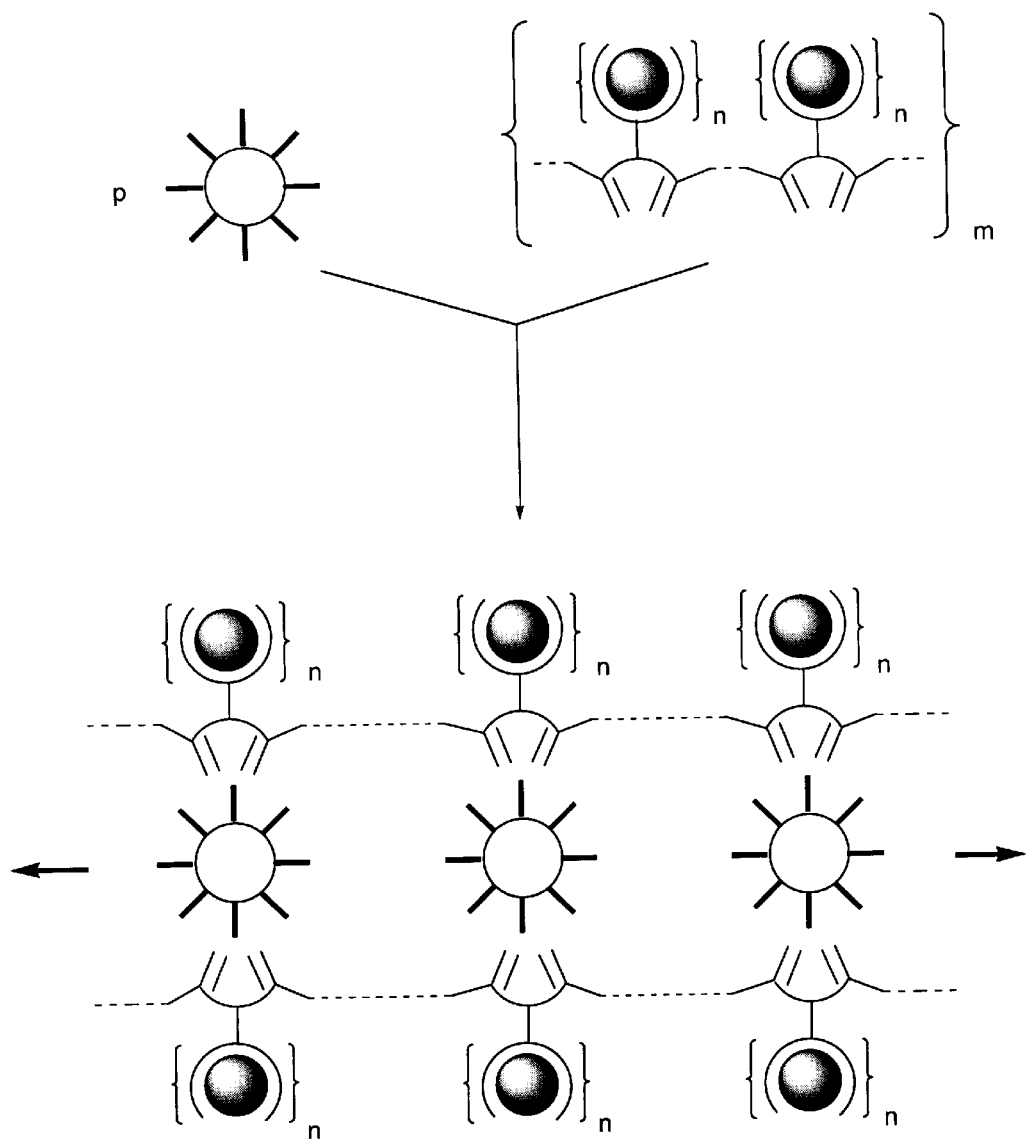
FIG. I.C

FIG. II
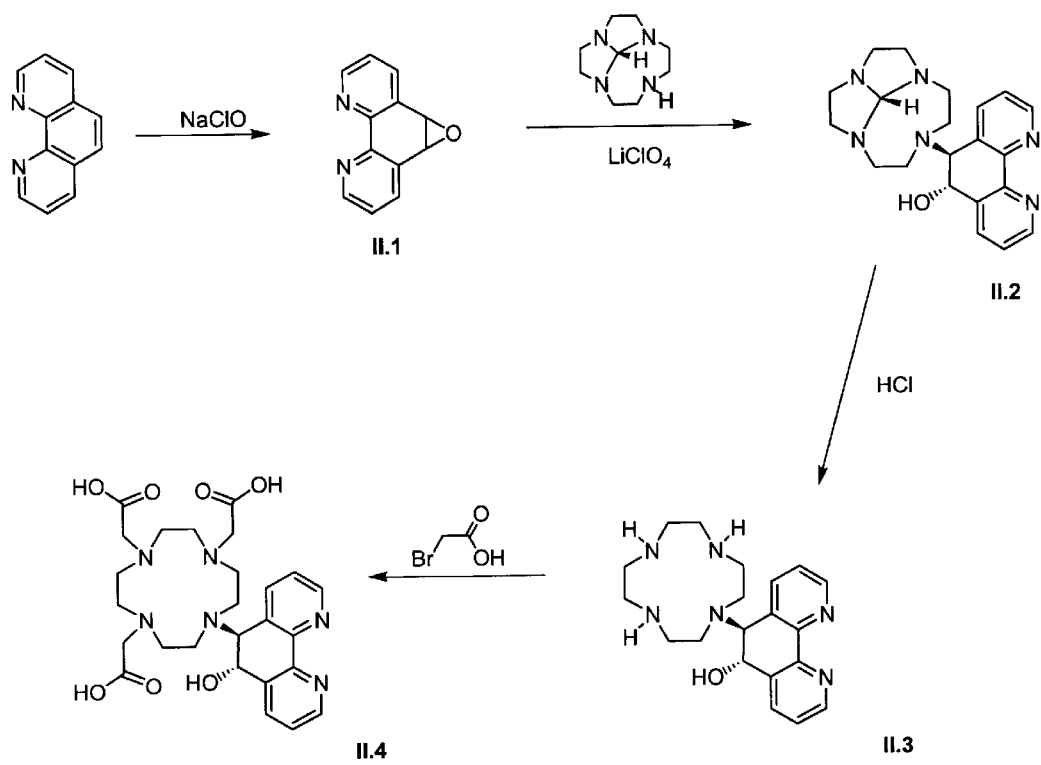

FIG. III
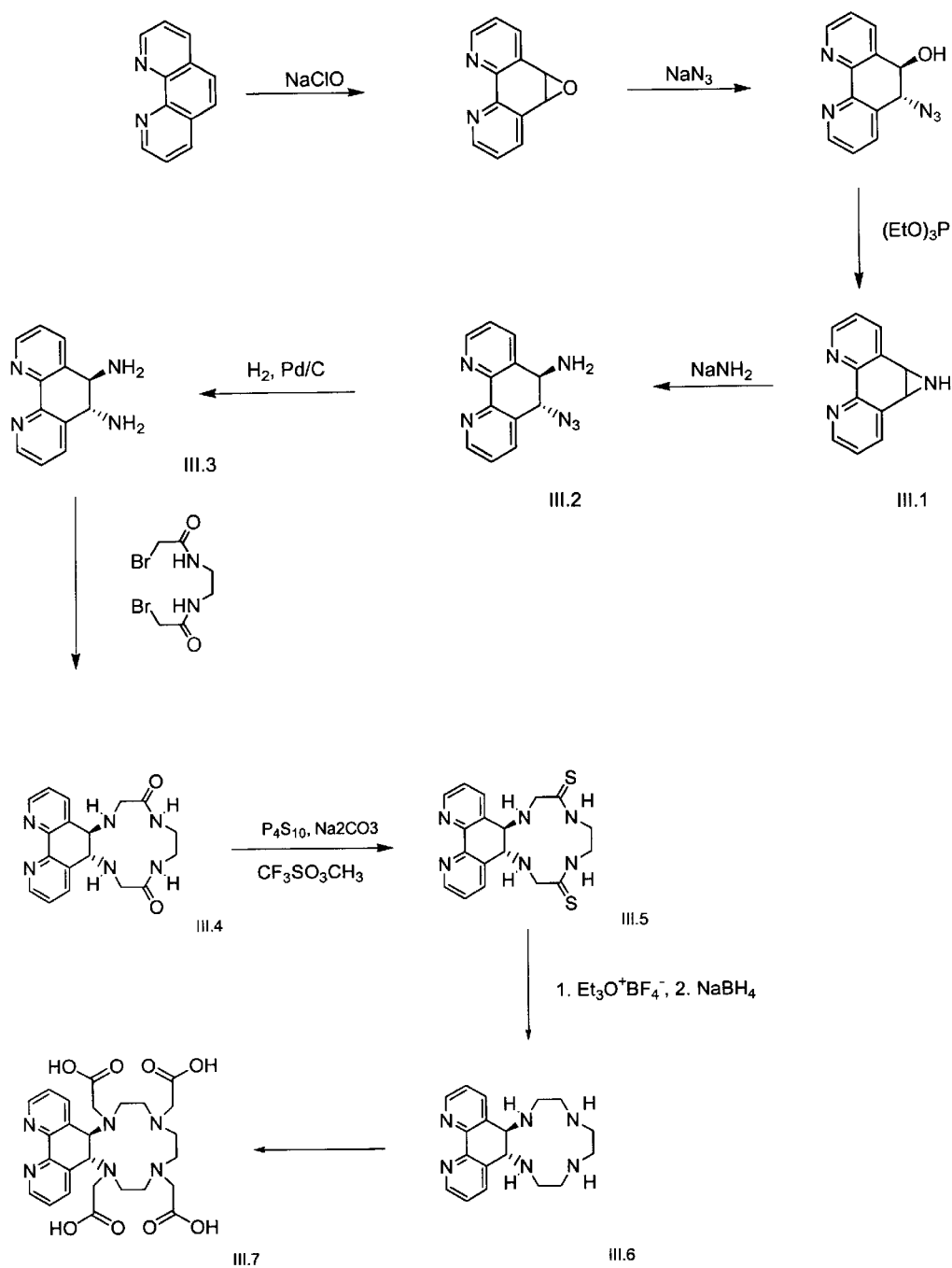

FIG. IV
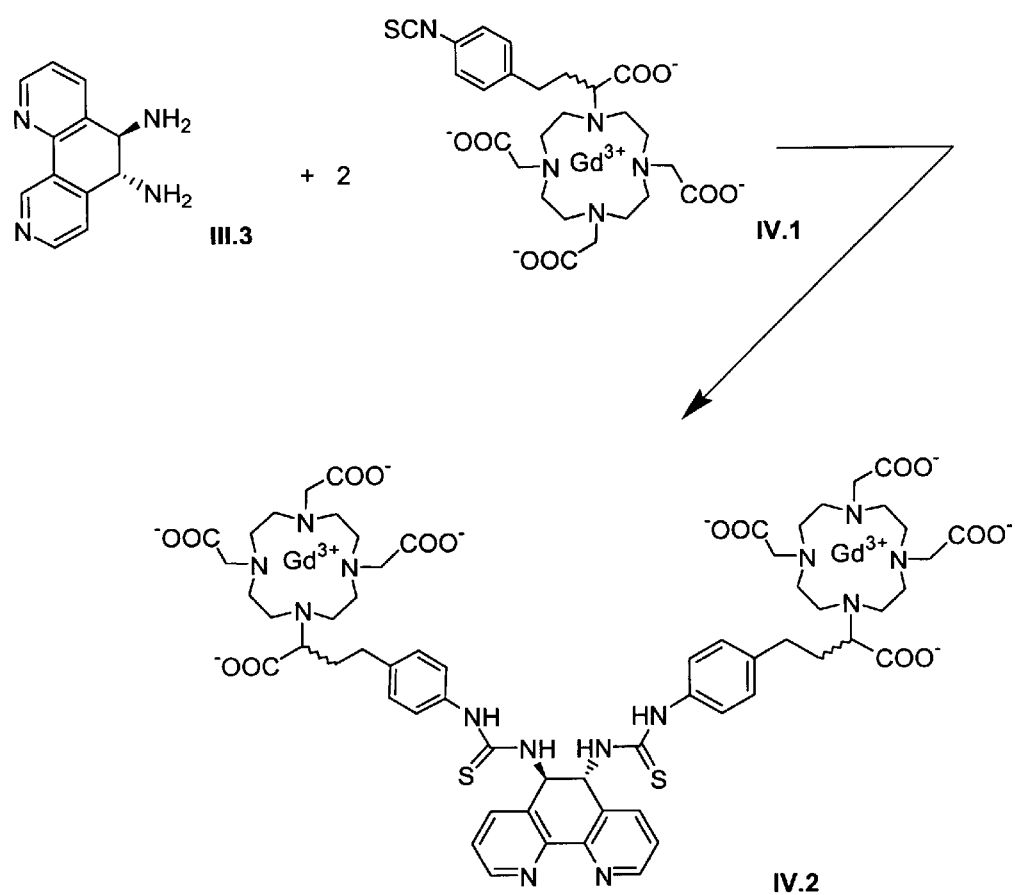

FIG. V.A
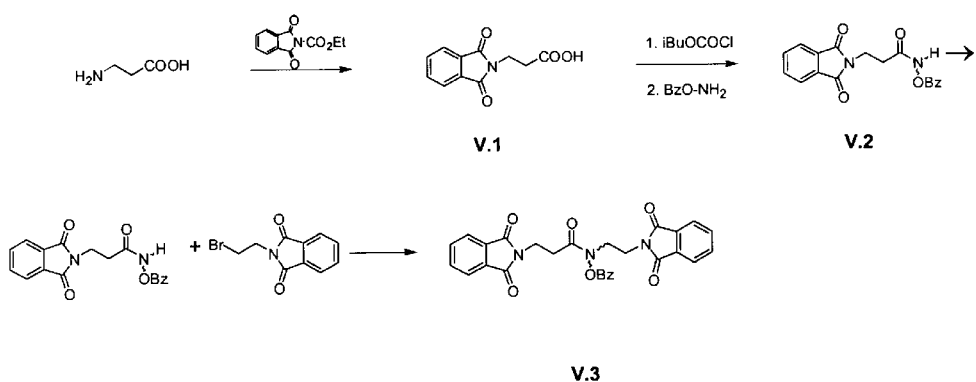
FIG. V.B
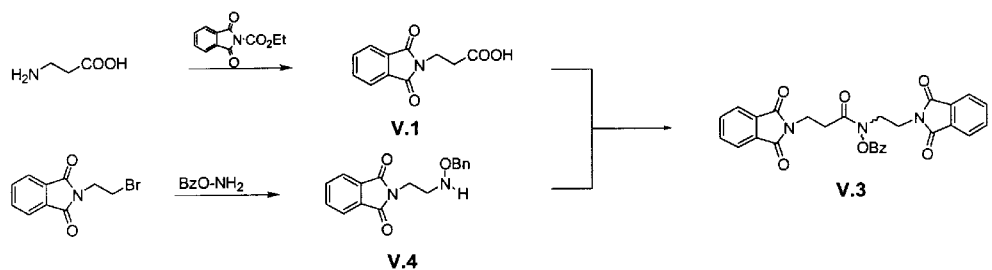

FIG. V.C
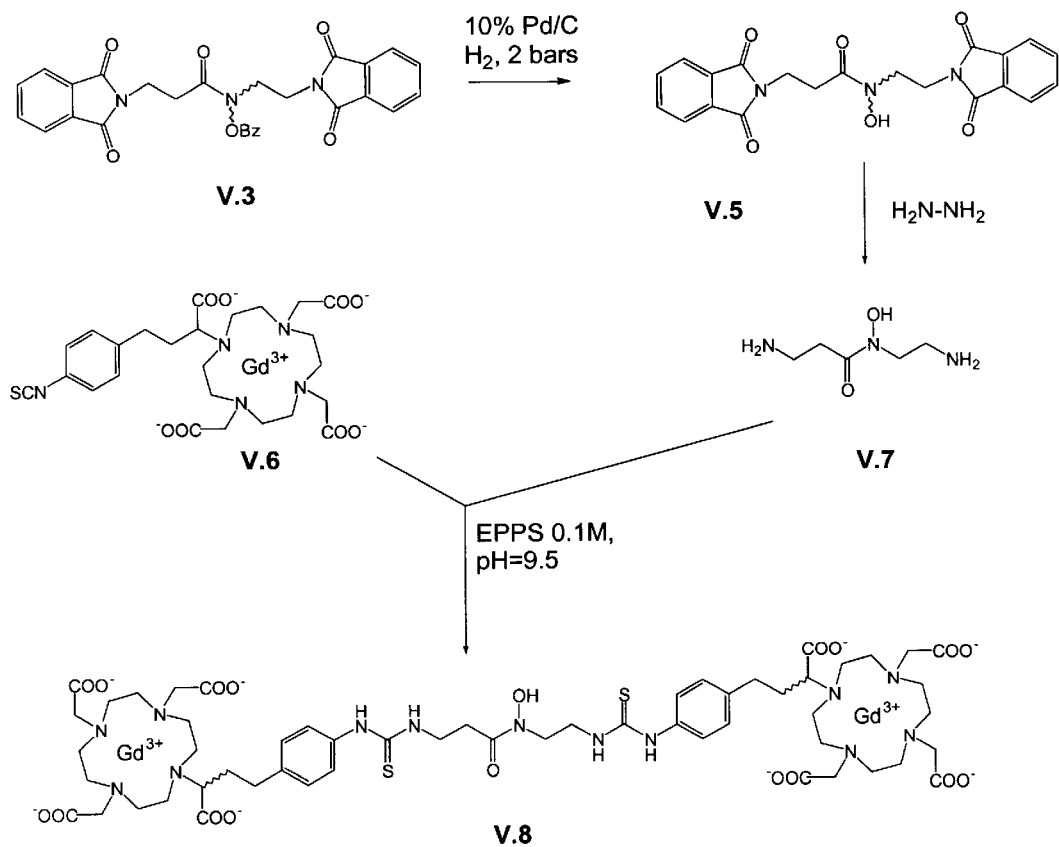

SELF-ASSEMBLING HETEROPOLYMETALLIC CHELATES AS IMAGING AGENTS AND RADIOPHARMACEUTICALS

BACKGROUND OF THE INVENTION

1. Field of the Invention

The present invention relates to diagnostic and therapeutic agents and compositions, methods of their use and processes for their preparation. More particularly, the invention relates to self-assembling heteropolymetallic chelates usefull for improving the contrast of x-ray, ultrasound, radionuclide and magnetic resonance (MR) images, and in therapeutic compositions.

2. Reported Developments

Metal chelates are useful for improving the contrast of X-ray, ultrasound, radionuclide and magnetic resonance (MR) images. Metal ions leading to an improvement of the contrast of medical images are usually too toxic to be injected as such and a wide variety of chelating ligands have been synthesized to ensure their complete elimination from the body. In all cases, the metal complexes must be thermodynamically stable and kinetically inert so as to limit dissociation in the body and the resulting toxicity as much as possible. New structures, either cyclic or linear, have been devised in recent years to achieve high stability and entirely new steric arrangements of heteroatoms such as N, O, P or S in aliphatic and/or aromatic frames have been suggested. Furthermore, reacting groups have been added to metal ligands so as to link them covalently or non-covalently to biological or synthetic macromolecules. A better tissue selectivity may then be achieved and special effects such as a higher relaxivity in MRI may be observed.

In MRI, highly stable chelates of paramagnetic ions are used to reduce the longitudinal and transverse relaxation times $T_1$ and $T_2$ of water (J. A. Peters et al., *Prog. Nucl. Magn. Reson. Spectrosc.* 1996, 28, 283). Various complexes of S state ions such as manganese(II), iron(III) and gadolinium(III) have received widespread attention. The $Gd^{3+}$ ion is the preferred paramagnetic species because of its high magnetic moment and its slow electronic relaxation times but, as mentioned above, it must be embedded into a chelating agent before being injected intravenously in order to reduce its toxicity. Gadolinium complexes provide information regarding blood-brain barrier impairments and myocardial perfusion abnormalities. They also allow the assessment of the vascular system (carotid arteries, renal and iliac arteries) and the imaging of the liver (see for instance V. M. Runge, *Diagn. Imag. Europ.* 37–45, 1997). The $Gd^{3+}$ ion has been successfully encapsulated by a variety of derivatives of DTPA (diethylenetriaminepentaacetic acid) or DOTA (1,4,7,10-tetraazacyclododecane-1,4,7,10-tetraacetic acid). Moreover, the structure of these ligands has been chemically modified in order to increase the hydrophobicity of their $Gd^{3+}$ complexes and thus favor an elimination through the liver and the bile rather than through the kidneys (J. F. Desreux et al., U.S. Pat. No. 5,358,704, 1993). The imaging of the liver is then greatly facilitated. Chemical alterations of the ligand structures have also been performed purposely to modify the physical parameters controlling relaxivity. The aim is to achieve a maximum relaxivity in the 5–60 MHz range which is the preferred frequency domain for imaging because of the better signal/noise ratio. For instance, covalent or non-covalent binding of a complex to a macromolecule leads to a reduction of its rotational correlation time and to a strong increase in relaxivity provided the macro-molecule and the $Gd^{3+}$ complex are rigidly linked together and rotate at about the same rate. In addition, the water exchange time between the inner coordination sphere of the metal ion and the bulk of the aqueous solution has been modified by altering structural features. Recently, amide groups in the DTPA unit have been shown to reduce the rate of exchange of water molecules(G. Gonzalez et al., *J Phys. Chem.* 98, 53–59, 1994). This reduction is detrimental to relaxivity when the chelate is associated to a macromolecule and should be avoided. Finally, it should be added that dysprosium(III) chelates have been found useful because of their very high magnetic moment (10.6 BM) that causes a loss of phase coherence and a pronounced reduction in signal intensity in $T_2$-weighted images.

Improving the contrast of X-ray images requires the use of chelates of metal ions that are able to absorb X-rays at least as well as iodine. These metallic ions should thus have atomic weights higher than 127 (for instance, the lanthanides, Ta, or Bi). Similar complexes can reflect or scatter ultrasound radiations sufficiently to alter the contrast of ultrasound images.

Radiopharmaceutical imaging makes use of short-lived radionuclides, such as $^{68}$Ga, $^{90}$Y, $^{99m}$Tc, $^{111}$In, $^{140}$La, $^{169}$Yb, $^{153}$Sm and others. After complexation with a suitable ligand, these isotopes are often linked covalently to biologically active macromolecules such as antibodies. Metal complexes have also been used extensively in therapy. For radiotherapy, α and β emitters of relatively short half-lives such as $^{67}$Cu, $^{90}$Y, $^{212}$Bi or $^{225}$Ac are strongly complexed by a ligand and are bound to an antibody. The chelates should not release their metal ions as the latter most often localize in the body and cause serious damage. For instance, free $^{90}$Y is known to concentrate in the bones where it causes myelosuppression and thus an increased risk of infection. Highly stable and kinetically inert metal chelates are thus desirable. In another medical application of metal chelates, $^{157}$Gd appears to be a promising agent for neutron capture therapy because of its very high thermal neutron capture cross section (J. L. Shih et al. *Med. Phys.* 19, 733–744, 1992) and again its use for curing tumors implies the formation of highly stable chelates.

The object of the present invention is a new approach to imaging and therapy with metal chelates that is illustrated schematically in FIGS. I.A–C.

SUMMARY OF THE INVENTION

Compounds of formula I, or pharmaceutically acceptable salts thereof are provided

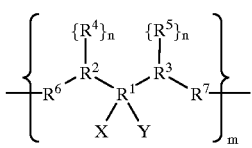

I wherein
n is 1 to 35, preferably 10 to 25;
m is 1 to 10;
X and Y are atoms that are able to coordinate metal ions selected from the group consisting of N, O, S and P;
$R^1$ is an aliphatic or aromatic skeleton to which X and Y are covalently linked and so designed as to ensure the formation of a highly stable metal complex. The organic skeleton is a straight-chain, branched, saturated or unsaturated hydrocarbon, preferably having 1 to 6 carbon atoms and most preferably 1 to 3 carbon atoms optionally substituted with oxygen or nitrogen, hydroxy or amino group(s);

Suitable X—$R^1$—Y units are mono-, di-, tri- or tetradentate assemblies, including derivatives of ortho-phenanthroline,

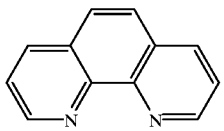

of an hydroxamic acid, of a β-diketone, of a Schiff base or imine, of a diphenol, of a 1,2-dione dioxime, of a dithiol, of 1-hydroxy-1,2-dihydro-pyridinone;

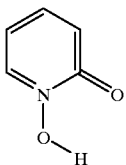

of pyridine-2-carboxaldehyde oxime
of N-hydroxy-2,6-dioxoperhydroazine

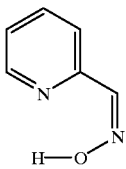

and of other ligands known to those skilled in the art to form stable metal complexes (A. E. Martell and R. M. Smith, NIST Critically Selected Stability

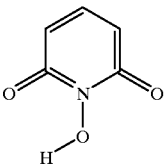

Constants of Metal Complexes Database, version 4.0, 1997);

$R^2$ and $R^3$ are independently amino, hydroxy, mercapto, imino, hydrazido, ester, ketone, aldehyde or carboxylic radicals (1 to 6, preferably one) to which ligands can be covalently linked; these radicals can be part of a straight-chain, branched, saturated (1 to 6 carbon atoms, preferably 1 to 3) or unsaturated (ethylenic moiety, 1 to 3 aromatic rings, preferably one) hydrocarbon unit;

$R^4$ and $R^5$ are independently ligands of a different type than X—$R^1$—Y and are able to strongly encapsulate other metal ions than the ones the X—$R^1$—Y unit can complex. These ligands must feature reactive functions that are to be covalently linked to $R^2$ and $R^3$, for example isothiocyanate, carboxylic, thiol, bromoacetyl groups or other chemical groups known to those skilled in the art.

Appropriate derivatives of DTPA and DOTA with side arms have been reported by several authors and are particularly suitable for that purpose as they form stable and kinetically inert lanthanide chelates. These compounds are well known to those skilled in the art. The $R^4$ and $R^5$ can contain a large number (1 to 35, preferably 10 to 25) of such compounds for example in an arborol architecture (see Zanini, D.; Roy, R. J. Org. Chem. 61, 7348–7354, 1996 as an example of synthesis of an arborol). The $R^{1-5}$ (X—Y) groups can also be one rigid chemical entity in which two different coordinating units are combined and are linked by one or several chemical bonds, for example a polyaminopolycarboxylic group and a phenanthroline unit. In that case the $R^2$ and $R^3$ groups are not necessarily needed.

$R^6$ and $R^7$ are independently H or straight-chain, branched, saturated (1 to 6 carbon atoms, preferably 2 to 4) or unsaturated (ethylenic moiety, 1 to 3 aromatic rings, preferably one) hydrocarbon unit with or without amino, amide, ester, imino, hydrazido groups or other groups needed to link together two or more $R^{1-5}$(X—Y) units well known to those skilled in the art.

In MRI imaging, the X—$R^1$—Y units must be devised in such a way that a highly stable complex will be formed spontaneously with one type of metal ions with atomic number Z in the range 21–31, 39–50, 72–79, ions such as $Fe^{2+}$, $Fe^{3+}$, $Co^{3+}$, $Mn^{2+}$, $Mn^{3+}$, $Cu^{2+}$, $Zn^{2+}$ being preferred in this invention. The $R^4$ and $R^5$ groups must form kinetically inert chelates with another type of metal ions with atomic number Z in the range 20–31, 38–50, 56–79, and $Gd^{3+}$ or $Dy^{3+}$ are preferred in this invention. In radiopharmacy, ions of nuclides such as $^{99m}Tc$, $^{111}In$, $^{62}Cu$, $^{68}Ga$ are preferred for encapsulation by the X—$R^1$—Y units and are used essentially for imaging while the radionuclides $^{90}Y$, $^{212}Bi$, $^{225}Ac$ and $^{188}Re$ are preferred for complexation by the $R^4$ and $R^5$ units and are used for therapy.

Also in accordance with the present invention, a method for diagnostic examination or therapeutic treatment of a mammal is provided.

In one aspect the method of the present invention comprises the steps of: administering to a mammal a composition comprising the self-assembled heteropolymetallic chelates contained in a pharmaceutically acceptable carrier; and monitoring the distribution of said heteropolymetallic chelates.

In another aspect the method of the present invention comprises the steps of administering to a mammal a composition comprising a radioactive metal complexed with the self-assembling heteropolymetallic chelates contained in a pharmaceutically acceptable carrier for radiotherapeutic treatment of said mammal and monitoring said treatment.

The self-assembling heteropolymetallic chelates may also be coupled with biomolecules, such as folates, for delivering the heteropolymetallic chelates into cells of an organ or tissue.

The self-assembling heteropolymetallic chelates can be administered through intravenous, intramuscular or intraperitonal routes in a physiologically acceptable medium, such as saline or water that is buffered or pH adjusted using physiologically acceptable salts or buffers well-known in the art.

BRIEF DESCRIPTION OF THE DRAWINGS

FIG. I.A shows several bidentate ligands, m=1 to 6, spontaneously associated around a single metal ion;

FIG. I.B shows several bidentate ligands, m=1 to 4, linked together and forming supramolecular entities around one metal ion;

FIG. I.C shows several bidentate ligands, m=1 to 4, linked together and forming supramolecular entities around several metals;

FIG. II shows the synthesis of 2-[4-[(5R*,6R*)-6-hydroxy-5,6-dihydro[1,10]phenanthroline-5-yl]-7,10-bis[2-hydroxy-2-oxoethyl]- 1,4,7,10-tetraazacyclododecan-1-yl] acetic acid, II.4;

FIG. III shows the synthesis of (10aR*,18bR*)-1,2,3,4,5,6,7,8,9,10,10a,18b-dodecahydro[1,4,7,10]-tetraazacyclododecino[2,3-f]][1,10]phenanthroline-1,4,7,10-tetraacetic acid, III.6;

FIG. IV shows the synthesis of-[4-({[((5R*,6R*)-6-{[(4-{4-hydroxy-4-oxo-3-[4,7,10-tris(carboxymethyl)-1,4,7,10-tetraazacyclododecan-1-yl]butyl}anilino)carbothioyl]amino}-5,6-dihydro[1,10]phenanthrolin-5-yl)amino]carbothioyl}amino)phenyl]-2-[4,7,10-tris(c arboxymethyl)-1,4,7,10-tetraazacyclododecan-1-yl]butanoic acid, gadolinium(III) chelate, IV.2;

FIG. V.A shows the synthesis of N-benzyloxy-N-(2'-phtalimidoethyl)-3-phtalimido-propanamide, V.3;

FIG. V.B shows the synthesis of N-benzyloxy-2-phtalimidoethylamine, V.4; and

FIG. V.C shows the synthesis of 4-[4-C{[({2-[(3-{[(4-{3-carboxy-3-[4,7,10-tris(carboxymethyl)-1,4,7,10-tetraazacyclododecan-1-yl]propyl}anilino)carbothioyl]amino}propanoyl)-(hydroxy)amino]ethyl}amino)carbothioyl]amino}phenyl)-2-[4,7,10-tris-(carboxymethyl)-1,4,7,10-tetraazacyclododecan-1-yl] butanoic acid; gadolinium(III) chelate, V.8.

DETAILED DESCRIPTION OF THE INVENTION

In this invention, one uses water-soluble ligands featuring chelating units of very different complexing abilities and represented above by the

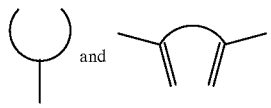

symbols respectively. Each bidentate complexing unit

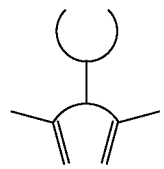

is behaving as either a separate chemical entity or several such units are linked together as shown by the—lines. In addition, the coordinating entity

is substituted by one or n>1 groups of the

type, for instance in a dendrimeric or arborol-type structure. In the above schemes, the first kind of chelating group must be a very selective complexing agent of a given type of metals, for instance lanthanide ions, represented here by the symbol

Thermodynamically stable and if possible kinetically inert complexes with metals of the type

are thus formed. The other chelating unit must display excellent and preferential complexing properties toward another kind of metals depicted above by the symbol

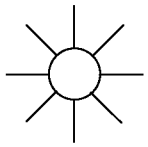

for instance, transition metal ions. The bidentate moieties

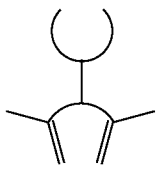

must be devised in such a way that they complex strongly and selectively one or several (n>1) metal ions of type

and then spontaneously form a high molecular weight and stable polymetaliic entity around one or several different metal ions of the

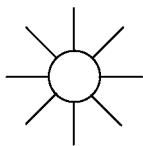

type.

The simplest case is illustrated in FIG. I.A where several bidentate ligands (m=1 to 6) spontaneously associate around a single metal ion. As shown in FIGS. IB and I.C, ligands featuring several bidentate units linked together can form supramolecular entities either around one metal ion (m=1 to 4) or around several metals (p≧2) in linear or closed chains (preferably three chains, m=3; two chains only are shown for clarity).

The invention described herein is thus based on a self-association process in which several organometallic entities spontaneously associate around several metal ions to form an entirely new heterometallic species of higher molecular weight. Self-association is defined here as the formation of a new chemical entity in water through the spontaneous association of chelating ligands complexed with metal ions of a given type. This process has to take place by coordination around one or several metal ions of another type due to the bidentate structure of the chelating agents. The new chemical entity must thus be formed by bringing together several organometallic species. Moreover, spontaneous is understood here as obtaining a new heteropolymetallic complex by simply mixing the aqueous solution of the salt of a metal of a given type with the aqueous solution of a bidentate complex of a metal of another type, possibly followed by pH adjustment and/or gentle heating.

This approach has distinct advantages:

1) due to a higher molecular weight and a larger molecular volume, slow rotational rates and thus higher relaxivities in MRI are achieved without further painstaking synthetic efforts since no new covalent bonds are needed to form a new species;
2) the association process and the preparation of the metallic complexes are taking place in water;
3) a strict control of the molecular weight is achieved;
4) heterometallic complexes are obtained; in these complexes, higher relaxivities in MRI may be reached if all metal ions are paramagnetic;
5) a radionuclide can be combined with paramagnetic ions in the same chelate thus allowing the simultaneous use of MRI and radioimaging and/or radioimmunotherapy;
6) two different radionuclides can be accommodated in the same chelate. In the scientific literature, the same distribution is assumed for two complexes with the same ligand, one of them containing a nuclide for imaging, for instance $^{111}$In, and the other one containing another nuclide suitable for therapy, for insance $^{90}$Y. This assumption and the painstaking process of preparing and testing two complexes with the same ligand are avoided here; and
7) bidentate chelates containing one type of metal ion and featuring a high affinity for another type of metal ion can be used for detecting that ion in vitro or in vivo either because of a change in relaxivity in MRI, a change of a spectroscopic property such as fluorescence or UV-visible absorption or a change in magnetism.

Only very few attempts at preparing heteropolymetallic self-assembling chelates suitable for imaging have been reported in the literature. S. Aime et al. reported (*Spectrochimica Acta* 49A, 1315, 1993) a study on the formation and the relaxivity properties of mixed $Gd^{3+}$—$Fe^{3+}$ chelates with a DTPA ligand featuring two amide groups derived from p-aminosalicylic acid. As indicated by these authors, this ligand does not allow the formation of a single solution species of well-defined stoichiometry. Moreover, the transformation of two carboxylic functions of DTPA into amide groups brings about a decrease in stability (P. Wedeking. et al., *Magn. Reson. Imaging* 1992, 10, 641). Another approach at preparing heterometallic complexes has been reported by C. Piguet et al (*Helv. Chim. Acta* 78, 1651–1672, 1995).These authors prepared poly-pyridine poly-benzimidazole ligands that form spontaneously mixed lanthanide(III)-Zn(II) or Fe(II) complexes in acetonitrile. However, complexes of different stoechiometries are formed simultaneously, these compounds are only sparingly soluble in water and organic solvents are needed to achieve sufficiently high thermodynamic stabilities. Moreover, several patents are dealing with the syntheses and the use in MRI of heteropolymetallic complexes formed by a porphyrin ring substituted by several polyaminopolyacetic ligands such as DTPA(G. Marchal et al., PCT Appl. WO 95 31219, 1995; U. Niedballa et al., U.S. Pat. No. 5,284,647, 1992). In contrast with the present invention, the complete organic skeleton of these ligands has to be synthesized prior to the binding of any metal ion and there is no self-associations of several organometallic units into one single species. In addition, the encapsulation of metal ions into the porphyrin ring most often requires rather drastic conditions such as keeping at the boiling point (153° C.) a solution of the ligand and the metal in dimethylformamide for several hours followed by a purification by chromatography. Finally, a number of patents and papers are devoted to the simultaneous use of two metal ions for imaging and/or therapy but in contrast to the present invention, the two metals are in different chemical entities. For instance, $Gd^{3+}$ and $Dy^{3+}$ chelates with the same ligand can be injected simultaneously to increase the contrast of MRI images (B. Dupas et al., *J Magn. Reson. Imaging* 1997, 7,472) or a $Gd^{3+}$ complex can be injected intravenously simultaneously with the oral administration of superparamagnetic iron oxide particles (for instance, N. O. Wallengren, *Acta Radiol.* 37, 791, 1996). In radiopharmacy, several authors have used simultaneously radioisotopes such as $^{111m}$In and $^{90}$Y but these isotopes were located in different complexes of the same ligand and it is assumed and it has been checked that the two complexes behave identically. In the present invention, ligands have been devised in such a way that only discrete, stable and water-soluble heteropolymetallic species of well-known stoichiometry are formed spontaneously. The stability and the molecular weight of these species are well-controlled by grafting in the same molecule two totally different complexing units aimed at achieving a selective coordination of metal ions with totally different steric requirements.

It is an object of this invention to provide new metal-chelating ligands.

It is an object of this invention to provide new metal ligands featuring two complexing entities with very different ligating properties.

It is an object of this invention to provide new ligands which are able to form highly stable water-soluble multimetallic chelates that spontaneously associate to one or several metal ions to form high molecular weight heteropolymetallic species.

Another object of the present invention is to provide metal chelating ligands which, when complexed with one or several metals heavier than iodine (e.g., Ba, Ta, Pb, Bi, lanthanides), are effective X-ray contrast agents.

Another object of the present invention is to provide metal chelating ligands which, when complexed with one or several gamma emitting radioactive nuclides (e.g. $^{299m}Tc$ or $^{111}In$), are effective as imaging radiopharmaceuticals.

Another object of the present invention is to provide metal chelating ligands which, when complexed with one or several alpha or beta emitting radioactive nuclides (e.g; $^{90}Y$, $^{153}Sm$, $^{188}Re$, $^{212}Bi$, $^{225}Ac$), become effective as therapeutic radiopharmaceuticals.

Another object of the present invention is to provide metal chelating ligands which form stable complexes with one or several radioactive nuclides that are effective for imaging (e.g. $^{299m}Tc$ or $^{111}In$) and with one or several other radionuclides that are effective for therapy (e.g. $^{67}Cu$, $^{90}Y$, $^{212}Bi$, $^{225}Ac$, $^{111}In$)

It is a further object of this invention to provide metal chelating ligands which, when complexed with one or several identical or different paramagnetic metal ions, are effective as relaxation catalysts in magnetic resonance imaging.

It is a further object of this invention to provide metal-chelating chelates that are thermodynamically stable, kinetically inert and, when desired, electrically neutral These, and other objects which will be appreciated by the practitioner of this invention, are achieved with compounds having the general formula I. The term "alkyl" as used herein alone or as part of another group, denote optionally substituted, straight and branched chain saturated hydrocarbon groups, preferably having 1 to 12 carbons in the normal chain, most preferably lower alkyl groups. Exemplary unsubstituted such groups include methyl, ethyl, propyl isopropyl n-butyl t-butyl isobutyl pentyl hexyl isohexyl heptyl 4,4-dimethylpentyl octyl 2,2,4-trimethylpentyl, nonyl decyl undecyl dodecyl and the like. Exemplary substituents include one or more of the following groups; halo, alkoxy, arylalkyloxy (e.g., benzyloxy), alkylthio, alkenyl alkynyl aryl cycloalkyl cycloalkenyl hydroxy, carboxyl (—COOH), amino, alkylamino, dialkylamino, formyl alkylcarbonyloxy, alkylcarbonyl, heterocyclo, aryloxy or thiol (—SH). Preferred alkyl groups are unsubstituted alkyl haloalkyl, arylalkyl aminoalkyl alkylaminoalkyl, dialkylaminoalkyl, alkoxyalkyl aryloxyalkyl, hydroxyalkyl and alkoxyalkyl groups.

The term "alkoxy" or "alkylthio" denote an alkyl group as described above bonded through an oxygen linkage (—O—) or a sulfur linkage (—S—), respectively. The term "alkylcarbonyl", as used herein, denotes an alkyl group bonded through a carbonyl group. The term "alkylcarbonyloxy", as used herein, denotes an alkyl group bonded through a carbonyl group which is, in turn, bonded through an oxygen linkage.

The term "cycloalkyl", as used herein alone or as part of another group denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl cycloheptyl cyclooctyl cyclodecyl cyclododecyl and adamantyl. Exemplary substituents include one or more alkyl groups as described above, and/or one or more groups described above as alkyl substituents.

The term "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl and naphthyl Exemplary substituents include one or more, preferably three or fewer, nitro groups, alkyl groups as described above, and/or one or more groups described above as alkyl substituents. Preferred aryl groups are unsubstituted aryl and hydroxyaryl.

The terms "halogen", "halo" or "hal", as used here in alone or as part of another group, denote chlorine, bromine, fluorine and iodine.

Reported herein are the syntheses of a few ligands whose structures have been devised in order to obtain molecular arrangements as illustrated in scheme I.

In a first example is reported the synthesis of a bidentate ligand containing a DOTA-like unit and a partially reduced ortho- phenanthroline group, (phen)HDO3A, II.

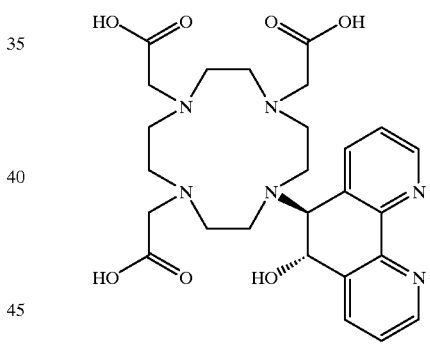

This ligand features a tetraazacyclododecane triacetic acid group that is known to form stable lanthanide chelates. The stability of the complex is further increased by the alcohol function which is a good coordinating group of the lanthanides as has been shown in the case of the ligand HPDO3A, 1,4,7-tris(carboxymethyl)-10-(2-hydroxypropyl)-1,4,7,10-tetraazacyclododecane (M. F. Tweedle, et al., U.S. Pat. No. 4,885,363, 1989). Moreover, the phenanthroline and bipyridine ligands are known to form highly stable tris-complexes with transition metal ions, particularly $Fe^{2+}$. The formation of a lanthanide complex with II is easily observed by nuclear magnetic resonance in the case of $Yb^{3+}$ because this ion induces paramagnetic shifts that cover 300 ppm. Moreover, a deep red color is immediately obtained on the addition of a $Fe^{2+}$ salt. The strong color change is a clear indication of the formation of a mixed Fe-lanthanide complex according to reaction

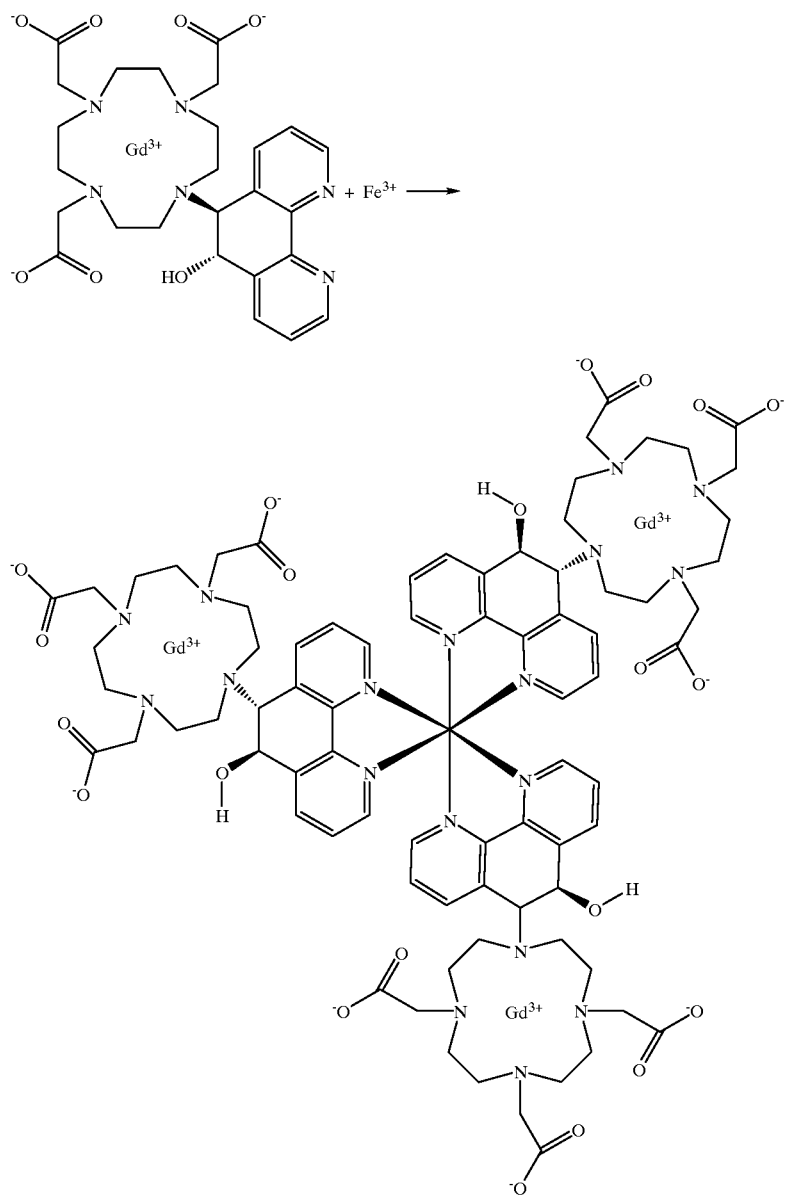

As expected, the relaxivity of the mixed $Fe^{2+}$—$Gd^{3+}$ chelate increases on formation of this heterometallic chelate. The formation of a mixed chelate is also easily followed by size-exclusion chromatography. Moreover, the luminescence of the $Tb^{3+}$ ion encapsulated by (phen)HDO3A is significantly increased. The synthesis of ligand II is illustrated in scheme II.

The preparation of another phenanthroline-DOTA type ligand, (phen)DOTA, III, is shown in FIG. III. In the (phen)DOTA ligand, the partially reduced phenanthroline ring is directly grafted onto the DOTA ligand and four carboxylic groups are available for the complexation of a lanthanide ion, This molecular arrangement ensures that the lanthanide complex will be highly stable. FIG. IV illustrates another approach to the preparation of heterometallic chelates featuring the 5,6-dihydro[1,10]phenanthroline-5,6-diamine ring and two DOTA derivatives. A variety of DOTA-type ligands can be used for this purpose and have been reported in the literature (see for instance D. D. Dischino et al., Inorg. Chem. 30, 1265–1269, 1991 or O. Renn et al., Bioconjugate Chem. 3, 563–569, 1992 or A. K. Mishra et al., Tetrahedron Lett. 37, 7515–7518, 1996). If needed, more DOTA or DTPA-type metal chelates can be added to trans-5,6-diamino-1,10-phenanthroline using arborols that feature one carboxylic group as an anchor and a large number of a amino groups. The synthesis of successive generations of such arborols has been reported in several scientific papers, one of which is D. Zanini et al. J, Org Chem. 61, 7348–7354, 1996.

Hydroxamic acids are a another group of chelating agents of interest in the present invention. These ligands form stable complexes with transition metal ions such as $Fe^{3+}$, $Zn^{2+}$, $Mn^{2+}$. The reactions leading to the synthesis of an hydroxamic acid substituted by two $Gd^{3+}$-DOTA derivatives are summarized in FIGS. V.A–C. Two methods have been developed for preparing compound V.3. from which N-benzyloxy-N-(2'-phtalimidoethyl)-3-phtalimidopropanamide, V.4, is readily obtained. Derivative V.4 is a good starting material for the synthesis of polymetallic chelates. In FIG. V.C, two DOTA-type $Gd^{3+}$ complexes have been covalently linked to V.4 using the N-[3-(p-aminophenyl)-1-carboxypropyl] derivative of 1,4,7,10-tetraazacyclododecane-N,N',N"-triacetic acid, a ligand whose synthesis has been reported by M. H. Ansari et al., *Bioorgan. Med. Chem. Lett.* 3, 1071–1072, 1993. Other similar chelates featuring an amino group available for binding have been described in the literature and are well-known to those skilled in the art. A larger number of $Gd^{3+}$ complexes can be linked to the two amine functions of V.4 with the help of arborols. Chelate V.6 rapidly forms a tris-complex with $Fe^{3+}$ as indicated by an increase in relaxivity and by the yellow color of its solutions.

All stereoisomers of the compounds and complexes of the present invention are contemplated herein, whether alone (that is, substantially free of other isomers), in a mixture of certain isomers (for instance as a racemate) or in any other mixture thereof.

The invention will now be further described by the following examples. These examples are illustrative rather than limiting.

EXAMPLE 1

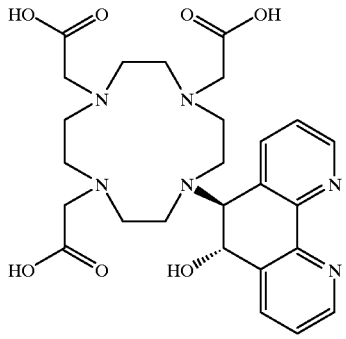

2-[4-[(5R*,6R*)-6-hydroxy-5,6-dihydro[1,10]phenanthrolin-5-yl]-7,10-bis(2-hydroxy-2-oxoethyl)-1,4,7,10-tetraazacyclododecan-1-yl]acetic acid, II.4

The synthetic procedure for obtaining this ligand is illustrated in FIG. I.

5,6-Oxirano-1,10-phenanthroline, II.1

No less than four scientific papers report on the synthesis of 5,6-oxirano-1,10-phenanthroline from 1,10-phenanthroline with yields ranging between 50 and 98% (see for instance Y. Shen et al, *Inorg. Chem.* 34, 6235–6236, 1995). The reported procedures are quite sensitive to experimental conditions such as pH, temperature or reaction times. The following procedure systematically afforded the pure epoxide in good yields.

A suspension of 1,10-phenanthroline (1 g, 5.55 mmol) in 150 ml of water was adjusted to 8.5. A fresh solution of 20 ml of sodium hypochlorite (Acros Organics USA, Pittsburgh, Pa. 15275-1126, 5% chlorine, 20 ml in 120 ml of water) was added in two portions while maintaining the pH at 8.5 after each addition. The reaction mixture was stirred at room temperature for 15 min while constantly adjusting the pH at 8.5 with a solution of sodium hydroxide. A small amount of phenanthroline that had not reacted and remained insoluble in the reaction mixture was eliminated by filtration. The filtrate was evaporated in a rotavapor and the residue was suspended in 150 ml of dichloromethane. After stirring overnight, the insoluble material was filtered off and the solvent was eliminated under vacuum Yield 72%; mp 159–161° C.

(5R*,6R*)-6-octahydro-7H-2a,4a,7,9a-tetraazacycloocta[cd]pentalen-7-yl-5,6-dihydro[1,10]phenanthrolin-5-ol, II.2

To a solution of 5,6-oxirano-1,10-phenanthroline (0.39g, 2 mmol) in 7 ml of thoroughly dried acetonitrile under nitrogen was added a solution of anhydrous lithium perchlorate (0.434 g, 4 mmol) in 0.8 mol of acetonitrile and a solution of 1,4,7,10-tetraazatricyclo[5.5.1.0.$^{4,13}$]tridecane (see M. F. Tweedle et al., *Europ. Pat.* 292 689, 1–31, 1998) in 3 ml of acetonitrile. The reaction mixture was refluxed with stirring for 31 h. The solvent was removed under vacuum leaving a brown oil that was immediately used in the next synthetic step without purification.

Mass spectrum (ES) 379 $(M+H)^+$.

(5R*,6R*)-6-(1,4,7,10-tetraazacyclododecan-1-yl)-5,6-dihydro[1,10phenanthrolin-5-ol, II.3

To the sample of compound II.2 obtained as above was added 40 ml of an hydrochloric acid solution (5 ml of 32% HCl in 50 ml of methanol). The solution was brought to reflux overnight. The precipitate which formed was collected by filtration and dried under vacuum, The resulting white solid was recrystallized from water and dried. Yield (tris-hydrochloride): 0.5 g, 52% for the synthesis of II.3 from II.1.

Melting point: 258° C. Mass spectrum (ES) 369 $(M+H)^+$.

2-[4-1(5S,6R)-6-hydroxy-5,6-dihydro[1,10]phenanthrolin-5-yl]-7,10-bis(2-hydroxy-2-oxoethyl)-1,4,7,10-tetraazacyclododecan-1-yl]acetic acid, II.4

Compound II.3 (1.0 g, 2.3 mmol) and anhydrous potassium carbonate (1.4 g, 7.6 mmol) were added to 50 ml of acetonitrile under nitrogen. The suspension was refluxed overnight with stirring. The hot solution was filtered to eliminate the insoluble material and the solvent was eliminated to yield an yellow solid deposit of the unprotonated polyamine. A solution of this polyamine in methanol (20 ml) was prepared under nitrogen. Another solution was prepared by slowly neutralizing bromoacetic acid (1.0 g, 7.2 mmol) with potassium hydroxide (0.4 g, 7.2 mmol) at 5° C. The two solutions were slowly mixed under nitrogen, 1.0 g (7.2 mmol) of potassium carbonate was added and the temperature was progressively raised to 40° C. Stirring was continued overnight at that temperature. An additional sample of potassium carbonate (1.0 g, 7.2 mmol) was added to the reaction mixture and the suspension was stirred at 65° C. for 6 h. After cooling, the precipitate was filtered off and the pH of the filtrate was adjusted to 2.5–3 with concentrated hydrochloric acid. The precipitate that formed rapidly was collected by filtration, washed with methanol and dried. It was recrystallized in the minimum amount of water. The filtrate was brought to dryness and dissolved in the minimum amount of hot ethanol. The insoluble material was collected by filtration and suspended in 5 ml of methanol. The insoluble inorganic salts were discarded and the solvent was eliminated yielding a second fraction of the desired product. The two solid fractions were dissolved in the minimum amount of water and passed onto a 1×10 cm column of a Dowexx2-200 ion exchanger conditioned in the $H^+$ form. The column was washed with 125 ml of water and then with 250 ml of 0.5 M ammonia The basic eluate was brought to dryness to yield a pale yellow material that was dissolved in the minimum amount of decarbonated water and added to a 1×10 cm column of a Dowex 1×2-200 ion-exchanger in the $OH^-$ form thermostated at 50° C. A gradient elution with formic acid solutions allowed the isolation of the sought compound in the 7.5 mmol formic acid fraction. Yield: 0.6 g, 48%.

Melting point: 245° C. decomposition, Mass spectrum (ES) 543 $(M+H)^+$.

Gadolinium(III) Chelate of Ligand II.4

The $Gd^{3+}$ chelate of ligand II.4 was prepared by adjusting the pH of a stoechiometric mixture of gadolinium trichloride and of II.4 in water. The complexation reaction was started at about pH 3 and the solution was heated to 65° C. for about 10 min. before each addition of a few drops of a diluted aqueous solutions of sodium hydroxide. The addition of base was stopped once the pH reached 6.5. The purity of the complex was checked by HPLC (C18 column, gradient A: 98% TRIS 50 mM EDTA, 10 mM—2% acetonitrile to B: 80% TRIS, 50 mM EDTA 10 mM—20% acetonitrile).

Carefully deionized water glassware cleaned with concentrated hydrochloric acid and deionized water were used throughout the whole procedure and precautions were taken to avoid contamination with traces of metals from metallic stands, clamps and mechanical agitators.

Mixed Gadolinium(III)—Transition Metal Chelate of Ligand II.4

Iron(II) tris-complex

A solution containing one equivalent of an iron(II) salt was mixed with a solution containing three equivalents of the gadolinium(III) chelate of II.4 with no pH adjustment. A deep red color appeared immediately and the reaction mixture was used as such after analysis of the iron and gadolinium content by inductively coupled plasma emission spectrometry.

Cobalt(III) tris-complex

The synthesis of the mixed $Co^{3+}$-$Gd^{3+}$ chelate was carried out using the carbonate salt $Na_3[Co(CO_3)_3].3H_2O$ as starting material. This compound was prepared as reported by H. Bauer et al., J. Am. Chem. Soc. 82, 5031–5032 (1960). The $Na_3[Co(CO_3)_3].3H_2O$ salt (0.036 g, 0.1 mmol) was dissolved in 10 ml of ethanol. To this solution was added 0.209 g (0.3 mmol) of the gadolinium chelate of ligand II.4. The mixture was refluxed for 1 h while adding drowpise 3 ml of a 0.1 HCl solution (0.3 mmol). The insoluble NaCl was removed by filtration and the filtrate was concentrated under vacuum. Crystals formed on cooling. The sought compound was purified in a water/ethanol mixture. Yield 82%, 0.17 g.

EXAMPLE 2

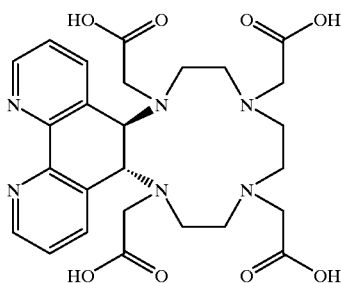

(10aR*,18bR*)-1,2,3,4,5,6,7,8,9,10,10a,18b-Dodecahydro-[1,4,7,10]tetrazacyclododecino[2,3-f] [1, 10]-phenanthroline-1,4,7,10-tetraacetic acid The approach followed for the synthesis of this ligand is presented in FIG. III (5R*,6R*)-6-Azido-5,6-dihydro-[1,10] phenanthroline-5-amine, III.2

1a,9b-Dihydroazirino[f][1,10]phenanthroline (III.1) was prepared as reported by Abu-Shqara, E. and Blum, J., Heterocycles, 1990, 27, 1197–1200). This aziridine (0.4 g, 2 mmol) was dissolved in a water (3 ml) ethanol (9 ml) mixture. Sodium azide (0.53 g, 8.2 mmol) and followed by ammonium chloride (0.44 g, 8.2 mmol) were added in one portion with stirring under nitrogen. The reaction mixture was refluxed for 18 h. The solid residue obtained after evaporation of the solvent under vacuum was dissolved in the minium amount of water. The aqueous solution was extracted thrice with 15 ml of chloroform The collected organic phases were dried over $MgSO_4$ and the solvent was evaporated to yield a pale brow oil (0.36 g, 75%).

Mass spectrum (ES) 239 $(M+H)^+$ (5R*,6R*)-5,6-Dihydro-1,10-phenanthroline-5,6-diamine, III.3

A solution of compound III.2 (0.36 g, 1.5 mmol) in 30 ml of ethanol was added to 50 mg of Lindlar catalyst (lead poisoned palladium on calcium carbonate) and stirred under 4 atm of hydrogen in a glass pressure reactor. After 48 h, the catalyst was eliminated by filtration and the solution was brought to dryness. The solid residue was dissolved in the minimum amount of hot methanol and concentrated hydrochloric acid was added dropwise until a until a slight precipitate was observed. The reaction mixture was left overnight at 0° C. The precipitate which formed was filtered off, washed with 5 ml of methanol and dried under vacuum, Yield 65%, beige solid.

Mass spectrum (ES) 213 $(M+H)^+$; mp 275° C., decomposition.

The unprotonated amine is easily obtained by stirring a suspension of its hydrochloride in $CHCl_3$ saturated with $NH_3$.

(10aR*,18bR*)-1,2,4,5,6,7,9,10,10a,18b-Decahydro-3,8-dioxo-[1,4,7,10]tetraazacyclododecino[2,3-f][1, 10]phenanthroline, III.4

Diamine III.3 (0.10 g, 0.47 mmol) was dissolved in acetonitrile dry (40 ml) and a solution of anhydrous N,N=-dibromoacetylethylenediamine (0.14 g, 0.47 mmol) in 20 ml of dry acetonitrile was added drowpise. Solid potassium iodide (0.03 g, 0.19 mmol) and potassium carbonate (0.65 g, 4.7 mmol) were added to the reaction mixture that was brought to boiling stirred during 30 h under nitrogen. After cooling, the insoluble material was filtered and washed with 10 ml of acetonitrile. All filtrates were brought together and the solvent volume was reduced by ⅓ by evaporation. A precipitate formed overnight at 0° C. It was filtered and dried under vacuum. Purification by recrystallization can be carried out in acetonitrile if the product is not pure. Yield 30%, 0.05 g.

Mass spectrum (ES) 353 (M+H)$^+$; mp 265° C.

(10aR*,18bR*)-1,2,3,4,5,6,7,8,9,10,10a,18b-Dodeeahydro-[1,4,7,10]tetraazacyclododecino[2,3-f] [1,10]phenanthroline, III.5

Diamide III.4 (0.06 g, 0.17 mmol) was suspended in 5 ml of 2-methoxyethyl ether freshly distilled over calcium hydride at 0° C. Sodium borohydride (0.064g, 1.7 mmol) was dissolved in 5 ml of 2-methoxyethyl ether, the solution was cooled at 0° C. and added to the suspension of compound III.4. Anhydrous trichloride (0.07 g, 0.56 mmol) was cautiously dissolved in 5 ml of 2-methoxyethyl ether at 0° C. This solution was added dropwise to the solution of III.4 while maintaining the temperature below 20° C. The reaction mixture was stirred overnight at 0° C. Water was added dropwise and stirring was continued during 1 hr at room temperature. The mixture was brought to dryness by evaporation and the remaining solid was suspended in methanol with stirring. After a few hours, the organic phase was separated by filtration and concentrated hydrochloride was added dropwise until a precipitate appeared. After one night at 0° C., the precipitate was collected and recrystallized repeatedly until the sought compound was purified, as checked by mass spectrometry. Yield 18%.

Mass spectrum (ES) 326 (M+H)$^+$ (10aR*,18bR*)-1,2,3,4,5,6,7,8,9,10,10a,18b-Dodecahydro[1,4,7,10]-tetraazacyclododecino[2,3-f] [1,10]phenanthroline-1,4,7,10-tetraacetic acid, III.6

Firstly, compound III.5, (80 mg, 0.26 mmol, isolated after neutralization of the hydrochloride with anhydrous potassium carbonate in dry acetonitrile) was dissolved in 20 ml of methanol. Secondly, bromoacetic acid (0.16 g, 1.14 mmol) was dissolved in methanol (5 ml) and slowly neutralized below 5° C. with 5 ml of methanol containing 0.06 g (1.14 mmol) of KOH. The two solutions were mixed, potassium carbonate (0.16 g, 1.14 mmol) was added in one portion and the suspension was stirred overnight at 15° C. under nitrogen. An additional sample of potassium carbonate (0.16 g) was added and stirring at 65° C. was continued during 6 h. After cooling, the insoluble material was filtered and washed with 5 ml of methanol. The pH of the collected filtrates was adjusted to 2.5–3 with concentrated hydrochloric acid and after stirring overnight at 0° C., the precipitate was filtered and recrystallized in water. Yield 60%, 0.08 g.

Mass spectrum (ES) 557 (M+H)

EXAMPLE 3

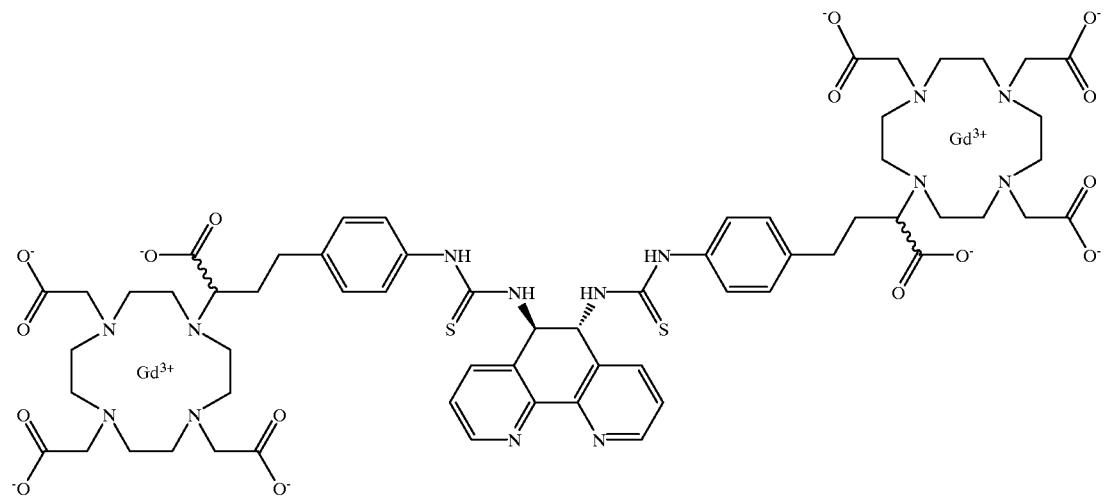

4-[4-({[((5R*,6R*)-6-{[(4-{4-hydroxy-4-oxo-3-[4,7,10-tris(carboxymethyl)-1,4,7,10-tetraazacyclododecan-1-yl]butyl}anilino)carbothioyl]amino}-5,6-dihydro[1,10]phenanthrolin-5-yl)amino]carbothioyl}amino)phenyl]-2-[4,7,10-tris(carboxymethyl)-1,4,7,10-tetraazacyclododecan-1-yl]butanoic acid, gadolinium(III) chelate, IV.2

The synthetic procedure for obtaining this ligand is illustrated in FIG. IV.

N-13-(p-isothiocyanatophenyl)-1-carboxypropyl)-1,4,7,10-tetraaza-N=,N@,N@=-tris(carboxymethyl) cyclododecane, gadolinium) salt, IV.1

N-[3-(p-aminophenyl)-1 -carboxypropyl)-1,4,7,10-tetraaza-N=,N@,N@=-tris(carboxymethyl)cyclododecane was prepared as reported by H. Ansari et al., *Bioorgan. Med. Chem. Lett.* 3, 1071–1072, 1993. A 0.04 M aqueous solution of this ligand is prepared by weighing. A aliquot of this solution is reacted with a freshly prepared suspension of a stoechiometric amount of gadolinium hydroxide. The reaction mixture is stirred at 80° C. until complete dissolution is achieved. The solution is evaporated and the remaining powder is used as such after verifying that the complexation is complete. ES-MS: 676.55; HPLC: elution with tris (hydroxymethyl)aminomethane 50 mM, EDTA 10 mM, pH 7 with 10% acetonitrile; C18 column, 0.5 ml/min flow, elution peak at 15 min.

The above Gd³⁺ chelate (0.312 g, 0.4585 mmol) was dissolved in 9 ml of water and 1.3 equivalent of thiophosgene Cl₂CS (67.6 mg, 44.82 µl) in 10 ml of CHCl₃ was added dropwise. After stirring overnight at room temperature, the aqueous phase was decanted and evaporated under vacuum at 40° C. The remaining solid was dissolved in a known volume of water and the resulting solution was kept at −18° C. The purity of the compound was verified by ES-MS: 718.62 and by HPLC after reaction with ethanolamine in EPPS (4-2-hydroxyethyl)-1-piperazinepropanesulfonic acid) buffer at pH 9.5, same gradient as above, elution peak at 25 min.

4-[4-({[((5R*,6R*)-6-{[(4-{4-hydroxy-4-oxo-3-[4,7,
10-tris(carboxymethyl)-1,4,7,10-
tetraazacyclododecan-1-yl]butyl}anilino)
carbothioyl)amino}-5,6-dihydro[1,10]phenanthrolin-
5-yl)amino]carbothioyl}amino)phenyl]-2-[4,7,10-tris
(carboxymethyl)-1,4,7,10-tetraazaeyclododecan-1-
yl]butanoic acid, gadolinium(III) chelate, IV.2

A 2.80 ml sample of a 59.34 mM solution of (5R*,6R*)-5,6-Dihydro[1,10]phenanthroline-5,6-diamine, III.3, in methanol was added to a 2.035 ml sample of a 0.1633 M aqueous solution of the isothiocyanato Gd³⁺ chelate IV.1. The reaction mixture became cloudy. Water (1 ml) was added and the pH was raised to between 6 and 7 by addition of a 0.1 M EPPS aqueous solution of pH 9.5. The reaction mixture was stirred at room temperature and the progress of the reaction was followed by HPLC (same conditions as above). After 6 h, HPLC chromatograms no longer evolved and a 5% excess (102 µl) of the gadolinium chelate solution was added. After stirring 3 h at room temperature, the ES-MS spectra contained peaks at M/2=825 for the disubstituted phenanthroline chelate (major peak) and at M=931 for the monosubstituted derivative. The insoluble material was collected by filtration, dried and suspended in absolute methanol After stirring overnight, the insoluble material was filtered and dried under vacuum Yield 66%. A clear aqueous solution of the chelate was obtained by addition of N-methyl-glucamine.

EXAMPLE 4

First Procedure for the Synthesis of N-benzyloxy-
N-(2'-aminoethyl)-3-aminopropanamide (scheme
V.A)
3-Phtalimido-propanoic acid (phtalimido-β-alanine), V.1

Sodium carbonate (6.0 g, 56.6 mmol) and β-alanine (5 g, 56 mmol) were dissolved in water (85 ml) and N-carbethoxyphtalimide (12.27 g, 56 mmol) was added in one portion to the vigorously stirred solution, The reaction was allowed to proceed until complete dissolution was achieved. Hydrochloric acid (25 ml, 2 M) was added and CO₂ was evolved. The sought product was isolated as a white precipitate after further addition of hydrochloric acid (20 ml, 6 M). It was filtered and dried under vacuum (8.04 g). A second crop was obtained by evaporating the filtrate and redissolving the residue in a mixture of water (20 ml) and 6hydrochloric acid (20 ml 6 M).

The two crops of phtalimido-β-alanine were combined. Yield: 9.57 g (78%), mp: 151–151.5° C.
N-benzyloxy-3-phtalimido-propanamide, V.2

O-benzylhydroxylamine hydrochloride (9 g, 56.4 mmol) was suspended in water (80 ml) and a solution of potassium hydroxide (3.16 g, 56.4 mmol) in water (40 ml) was added dropwise. The clear basic solution was extracted twice with diethylether (60 ml). The ether extracts were combined, dried over magnesium sulfate. The inorganic salt was eliminated by filtration and the solvent was evaporated under reduced pressure. The free O-benzylhydroxylamine (6.76 g, 54.8 mmol, 97%) was obtained as a colorless liquid.

Phtalimido-β-alanine (V.1) (8 g, 36.5 mmol) was dissolved in tetrahydrofuran (100 ml dried over potassium and distilled) in dry glassware under nitrogen. Triethylamine (5.32 ml, 38.3 mmol, 5% excess) was added dropwise and the reaction mixture was cooled down to −15° C. under stirring. A solution of iso-butyl chloroformate (3.72 ml, 38.3 mmol) in dry tetrahydrofuran (5 ml) was added dropwise while the temperature was maintained at −15° C. and O-benzylhydroxylamine (4.49 g, 36.5 mmol) was added at the same temperature 15 minutes later. The reaction was allowed to proceed for 3 hours at −15° C. then overnight at room temperature. The white precipitate which formed was filtered and washed with tetrahydrofuran. After drying, this precipitate was suspended and stirred in hot water (100 ml). After a few minutes, the insoluble material was collected by

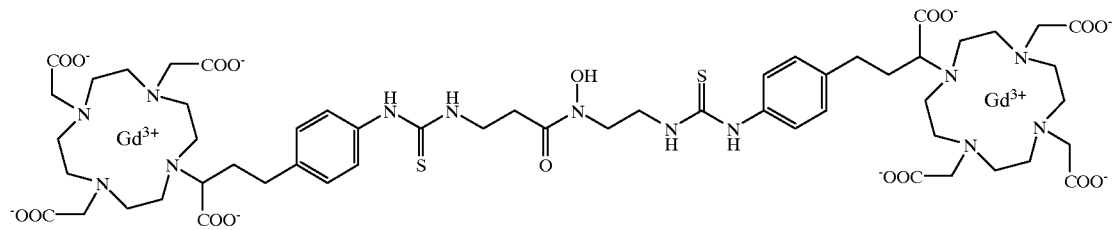

4-(4-{[({2-[(3-{[(4-{3-carboxy-3-14,7,10-tris
(carboxymethyl)-1,4,7,10-tetraazacyclododecan-1-
yl]propyl}anilino)carbothioyl]amino}propanoyl)
(hydroxy)amino]-ethyl}amino)carbothioyl]
amino}phenyl)-2-[4,7,10-tris(carboxymethyl)-1,4,7,
10-tetraazacyclododecan-1-yl]butanoic acid;
gadolinium(III) chelate, V.8

The synthetic procedure followed for obtaining this ligand is illustrated in scheme V.A-C. Two procedures were used to prepare N-benzyloxy-N-(2'-aminoethyl)-3-aminopropanamide, V.3 as illustrated in FIG. V.A and V.B respectively.

filtration and washed with hot water. It was dried and recrystallized in hexane/ethyl acetate. Moreover, the tetrahydrofuran filtrate obtained at the end of the reaction was evaporated and the residue was taken up in dichloromethane (100 ml). This solution was extracted with 5% sodium carbonate (twice 50 ml), then with 5% citric acid (twice 50 ml) and finally dried over magnesium sulfate. The inorganic salts were discarded and the solvent was evaporated under reduced pressure. The remaining white product was recrystallized in hexane/ethyl acetate. The purity of the two solids was checked before combining them in a single sample. Yield 9.51 g (80%) of the title compound (mp:143–143.5° C.). TLC (silica, dichloromethane/methanol 9:1) Rf: 0.86.

N-benzyloxy-N-(2'-phtalimidoethyl)-3-phtalimido-propanamide, V.3

N-benzyloxy-3-phtalimido-propanamide (V.2) (1.0 g, 3.08 mmol) was dissolved in N,N-dimethylformamide (10 ml, dried over molecular sieves). Sodium hydride (0.15 g of a 60% oil dispersion thoroughly washed with hexane and decanted) was added to this solution and the mixture was stirred under nitrogen for one hour. A solution of N-bromoethylphtalimide (1.66 g, 6.16 mmol) was added dropwise and the resulting solution was heated at 100° C. and stirred at this temperature for two days. The cooled mixture was then poured on ice/water (about 20 ml) and the aqueous phase was extracted with ethyl acetate (three times 25 ml). The organic solutions were combined, dried over magnesium sulfate and after filtration, the solvent was evaporated on a rotary evaporator. The crude product was purified by column chromatography on silica by eluting firstly with dichloromethane/hexane(1:1) to eliminate N-ethylene phtalimide and secondly with hexane/ethyl acetate (1:1). The fractions containing the pure compound were evaporated to yield 0.34 g of a colorless glassy solid. Part of the reagent N-benzyloxy-3-phtalimido propanamide (V.2) (0.31 g) was also recovered. Yield : 32% (based on the quantity of reagent that effectively reacted), mp: 143° C. TLC (silica, hexane/ethyl acetate 1:1) Rf: 0.23 (the O-substituted analogue of V.3 had a Rf value of 0.30).

Second Procedure for the Synthesis of N-benzyloxy-N-(2'-aminoethyl)-3-aminopropanamide (scheme V.B)

Synthesis of N-benzyloxy-2-phtalimidoethylamine, V.4

Neat neutralized O-benzylhydroxylamine (4.54 g, 36.9 mmol) obtained as reported above was mixed with pure 2-bromoethylphtalimlde. The liquid mixture was stirred at 80° C. under nitrogen during 48 hours. Absolute methanol (11 ml) is added. The white crystalline solid that separated was collected by suction filtration and washed with cold methanol (2 ml). The solid was dried under vacuum and was recrystallized in methanol Yield: 2.99 g (57%).

Melting point: 258° C. Mass spectrum (ES) 296.7 $(M+H)^+$.

N-benzyloxy-N-(2'-phtalimidoethyl)-3-phtalimido-propanamide, V.3

3-Phtalimido-propanoic acid (IV.1) (0.74 g, 3.375 mmol) was dissolved in tetrahydrofuran (15 ml, dried over potassium and distilled) under nitrogen, Triethylamine (0.494 ml, 3.54 mmol, 5% excess) was added to this solution and the mixture was cooled to −15° C. iso-Butyl chloroformate (0.46 ml, 3.54 mmol in 5 ml dry tetrahydrofuran) was added dropwise while maintaining the temperature at −15° C. After 15 minutes, N-benzyloxy-2-phtalimidoethylamine (IV.5) (1 g, 3.375 mmol in 10 ml dry tetrahydrofuran) was added dropwise at −15° C. and under nitrogen. The mixture was stirred during 3 hours at −15° C. and at room temperature overnight. The solvent was evaporated under reduced pressure and the residue was taken up in ethyl acetate (25 ml). The solution was extracted with water (25 ml), saturated sodium carbonate (25 ml), water (25 ml), 1M hydrochloric acid (25 ml), water (25 ml) and brine (25 ml). The organic solution was dried over magnesium sulfate, filtered and evaporated. The remaining white residue was recrystallized in hexane/ethyl acetate. The title compound was isolated as white crystals that were dried under vacuum. Yield: 53%

Preparation of the Gadolinium(III) Complex V.8
N-hydroxy-N-(2'-phtalimidoethyl)-3-phtalimido-propanamide, V.5

N-benzyloxy-N-(2'-phtalimidoethyl)-3-phtalimido-propanamide, V.3 (500 mg, 1.005 mmol), was dissolved in 50 ml of methanol at 70° C. The solution was poured in a hydrogenation apparatus and 170 mg of 10% Pd/C was added. The mixture was stirred under hydrogen (2 bars) for 25 min at 70° C. The catalyst was filtered and the solution evaporated to leave the title compound as a white glassy solid. Yield: quantitative. TLC (silica, hexane/ethyl acetate 1/1, aqueous $FeCl_3$ detection; Rf=0.1)

ES-MS: 408.4 $(MH^+)$

N-hydroxy-N-(2'-aminoethyl)-3-amino-propanamide, V.7.

N-hydroxy-N-(2'-phtalimidoethyl)-3-phtalimido-propanamide, V.5 (400 mg, 0.982 mmol), was dissolved in absolute ethanol (20 ml). Hydrazine hydrate (5 equiv, 4.9 mmol, 245 mg) was cautiously added and the mixture was refluxed under nitrogen for two hours. It was then left overnight at room temperature. The precipitated phtalazone was suction-filtered and the white solid was washed with fresh ethanol (2×5 ml). The filtrate was evaporated under reduced pressure and dried overnight under vacuum at room temperature. The glassy solid was finally redissolved in deionized water (10 ml) and the solution was aliquoted in several plastic vials, frozen and stored at −20° C. Yield: quantitative ES-MS: 148.2 $(MH^+)$.

4-(4-{[({2-[(3-{[(4-{3-carboxy-3-[4,7,10-tris(carboxymethyl)-1,4,7,10-tetraazacyclododecan-1-yl]propyl}anilino)carbothioyl]amino}propanoyl)(hydroxy)amino]ethyl}amino) carbothioyl]amino}phenyl)-2-[4,7,10-tris(carboxymethyl)-1,4,7,10-tetraazacyclododecan-1-yl]butanoic acid; gadolinium(II) chelate, V.8.

A 0.148 solution of N-hydroxy-N-(2'-aminoethyl)-3-amino propanamide (V.7) in water (50 μl) was mixed with 850 μl of a solution of 4-(2-hydroxyethyl)-1-piperazinepropanesulfonic acid (0.1M) in water at pH=9.5. A 0.1633 M solution of the isothiocyanato gadolinium(III) chelate V.6 in water (100 μl, 2.2 equiv) was added and the mixture was stirred for an hour at room temperature. The reaction was monitored by HPLC (C18 analytical column; solvent A: 90% tris 50 mM, EDTA 10 mM, pH=7 and 10% acetonitrile; solvent B: acetonitrile; gradient: 0 min, 90% A; 30 min, 40% A; 35 min, 40% A; 40 min, 90% A; 45 min, 90% A; retention time: 14 min). Once the reaction was complete, the solution was loaded onto a G15 GPC column (40×1 cm) and eluted with water. Fractions (0.5 ml) were collected and analyzed by recording their UV absorbance at 254 nm, The bisthiourea IV.8 was isolated in the fist fractions and was characterized by its negative ion electrospray mass spectrum (peak at 837.5 for $M^{2-}/2$). The product was stored as a water solution in a freezer at −20° C.

For radiopharmaceutical or radiotherapy applications it is convenient to prepare the self-assembling heteropolymetalic chelates of the present invention at, or near, the site where they are to be used. A single, or multi-vial kit that contains all of the components needed to prepare the complexes of this invention, other than the radionuclide ion itself is an integral part of this invention.

The amount administered may be selected based on the desired use, such as to produce a diagnostic image of an organ or other site of a subject or a desired radiotherapeutic effect, by methods known in the art. Exemplary dosages are those employing about 2–200 mCi rhenium (for radiotherapy) or about 10–60 mCi technetium (for imaging). The "subject" of the methods of the present invention is preferably a mammal such as a domestic mammal, for example, a dog, cat, horse or the like, or most preferably, a human.

Rhenium is particularly useful as a radiotherapy agent. The rhenium employed is preferably one of the radionuclides Re-186 or Re-188, or a mixture thereof which mixture may also include Re-185 and/or Re-187. Preparation of the complexes of the present invention where the metal is rhenium may be accomplished using rhenium in the +5 or +7 oxidation state. Examples of compounds in which rhenium is in the Re(VII) state are $NH_4ReO_4$ or $KReO_4$. Re(V) is available as, for example, $[ReOCl_4]$ (NBu4), $[ReOCl_4]$ ($AsPh_4$), $ReOCl_3$ ($PPh_3$) and as $ReO_2$ $(Pyridine)_4$+. (Ph is phenyl; Bu is n-butyl). Other rhenium reagents capable of forming a rhenium complex may also be used.

Technetium is particularly useful as a diagnostic imaging agent. The technetium employed is preferably one or more of the radionuclides Tc-99m, Tc-94m or Tc-96. The preferred radioisotope for medical imaging is $^{99m}Tc$. Its 140 keV γ-photon is ideal for use with widely-available gamma cameras. It has short (6 hour) half life, which is desirable when considering patient dosimetry. $^{99m}Tc$ is readily available at relatively low cost through commercially-produced $^{99}Mo/^{99m}Tc$ generator systems. Preparation of the complexes of this invention where the metal is technetium may be accomplished using technetium in the form of the pertechnetate ion. For Tc-99m, the pertechnetate ion is preferably obtained from commercially available technetium-99m parent-daughter generators; such as technetium is in the +7 oxidation state. The generation of the pertechnetate ion using this type of generator is well known in the art, and is described in more detail in U.S. Pat. Nos. 3,369,121 and 3,920,995. These generators may generally be eluted with saline solution, and the pertechnetate ion obtained as the sodium salt. Pertechnetate may also be prepared from cyclotron-produced radioactive technetium using procedures well know in the art.

The single-vial kit of the present invention comprises the heteropolymetallic complex and a source of a pharmaceutically acceptable reducing agent such as a stannous salt. Preferably, in addition, the kit is buffered with a pharmaceutically acceptable acid or base to adjust the pH to a desired value for complex formation. It is preferred that the kit contents be in lyophilized form. Such a single vial kit may optionally contain exchange ligands such as glucoheptonate, gluconate, mannitol malate, citric or tartaric acid and may also contain reaction modifiers, such as diethylenetriaminepentaacetic acid or ethylenediamine tetraacetic acid. Additional additives, such as solubilizers (for example α-, β- or γ-cyclodextrin), antioxidants (for example ascorbic acid) and/or fillers (for example, NaCl) may be employed to improve the radiochemical purity and stability of the final product, or to aid in the production of the kit.

A multi-vial kit of the present invention comprises, in one vial, the components, other than the radionuclide itself, required to form a labile radionuclide (especially Tc(V)) complex, that is, an exchange ligand and a pharmaceutically acceptable reducing agent such as a stannous salt. The heteropolymetallic complex is contained in a second vial as well as optional additives such as buffers appropriate to adjust the pH to its optimal value.

A single vial kit may be ready for use following addition of the radionuclide ion, such as pertechnetate. A multi-vial kit may be ready for use by addition of the radionuclide ion, such as pertechnetate, to the vial containing exchange ligand and reducing agent, and after waiting an appropriate period of time for formation of a labile complex, the contents of this vial are added to the second vial containing a source of the desired ligand. After a reaction time of about 1 to 60 minutes, the complex of the present invention is formed. It is advantageous that the contents of both vials of this multi-vial kit be lyophilized. As described for the single vial kit, additional additives may be employed to improve the radiochemical purity and stability of the final product, or to aid in the production of the kit.

Having described the invention, it is understood that changes and modifications may be effected within the spirit and scope of the invention

What is claimed is:

1. A compound of formula I having the structure or a pharmaceutically acceptable salt thereof

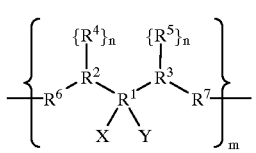

I wherein $X$—$R^1$—$Y$ represent a first chelating group and $R^4$ and $R^5$ represent a second chelating group which is covalently linked to $X$—$R^1$—$(R^2$—$R^6$, $R^3$—$R^7)$—$Y$ through $R^2$ and $R^3$, wherein X and Y are independently atoms which coordinate metal ions selected from the group consisting of N, O, S, and P;

$R^1$ is an aliphatic or an aromatic skeleton to which X and Y are covalently linked selected from the group consisting of straight-chain, branched, saturated or unsaturated hydrocarbons optionally substituted with oxygen, nitrogen, hydroxy or amino groups;

$R^2$ and $R^3$ are independently amino, oxy, mercapto, imino, hydrazido, ester, ketone, thiourea, aminoacetyl; or a saturated or unsaturated hydrocarbon substituted with amino, amido, oxy, mercapto, imino, hydrazido, ester, ketone, thiourea or aminoacetyl;

$R^4$ and $R^5$ are independently a ligand nucleus selected from the group consisting of a cyclic or a non-cyclic linear or branched hydrocarbon having one to 6 nitrogen atoms, one of which at least is substituted by one carboxylate, phosphonate, oximate, diketonate, azino or hydroxamate group, said ligand nucleus optionally having one to six oxygen, sulfur or phosphorous atoms; said $R^4$ and $R^5$ ligand nucleus forming a complex with a metal atom different from the metal atom formed with $X$—$R^1$—$Y$;

$R^6$ and $R^7$ are independently H, or straight-chain, branched, saturated or unsaturated hydrocarbons; or straight-chain, branched, saturated or unsaturated hydrocarbons substituted with amino, amide, ester, imino or hydrazido;

n is 1 to 35; and m is 1 to 10.

2. A compound of claim 1 wherein $X$—$R^1$—$Y$ together are

[Structure: partially reduced phenanthroline with Q₁ and Y₁ substituents]

wherein
Y₁ is —OH, O-alkyl, —SH, amide, NH-alkyl or NH-aryl;
Q₁ is a ligand nucleus covalently linked to the partially reduced phenanthroline ring and selected from the group consisting of a cyclic or non-cyclic linear or branched hydrocarbon having one to six nitrogen atoms with at least one of the nitrogen atoms substituted by one carboxylate, phosphonate, oximate, diketonate, azino or hydroxamate group, or with at least one $R_1$ group; and
$R_1$ is hydrogen, alkyl, arylalkyl, aryl, or $$-CH_2-\overset{\overset{O}{\|}}{C}-NR_2R_3$$

wherein $R_2$ and $R_3$ are independently hydrogen, alkyl, arylalkyl or aryl; or
$R_1$ is

[structures: —(CH₂)ₘ—phenyl(R₁₀,R₁₁) or —(CH₂)ₚ—CH(R₄)—X₁]

wherein $R_4$ is hydrogen, alkyl, arylalkyl, aryl, alkoxy or hydroxyalkyl, or

[structure: —(CH₂)ₘ—C(=O)—N(R₄)—A₁—phenyl(R₁₀,R₁₁)]

wherein $R_{10}$ and $R_{11}$ are each independently hydrogen, alkyl, —NO₂, $$-NH_2, -NH-\overset{\overset{S}{\|}}{C}-NH-R_4, -NCS \text{ or } -\overset{\overset{O}{\|}}{C}-NR_4R_{12};$$

$R_{12}$ is hydrogen, hydroxyalkyl, alkoxy, alkyl, aryl or arylalkyl;
$A_1$ is —(CH₂)_q-, —(CH=CH)—, —(CH=CH)₂- or a single bond; each —(CH₂)_q- is independently substituted with alkyl or hydroxyalkyl;
$X_1$ is —COOZ₁, PO₃(Z₁)₂ or —CONHOZ₁, —SO₃Z₁ wherein $Z_1$ is a hydrogen atom or a cation;
m is an integer from 0 to 3;
p is an integer from 0 to 3; and
q is an integer from 1 to 5.

3. A compound of claim 2 wherein
$Q_1$ is 1,4,7,10-tetraazacyclododecane, 1,4,8,11-tetraazacyclo-tetradecane, ethylenediamine, diethylenetriamine and triethylenetetramine substituted by at least one amincarboxylate, aminophosphonate or aminohydroxamate.

4. A metal chelate comprising a compound of claim 1 complexed with a first metal and a second metal wherein:
said first metal being selected from atoms having an atomic number of 21 to 31, 39 to 50 or 72 to 79 forms a highly stable complex with the X—R¹—Y unit contained in said compound, and said second metal being selected from atoms having an atomic number of 21 to 31, 38 to 50 and 56 to 79 forms a kinetically inert chelate with the $R^4$ and $R^5$ unit contained in said compound, wherein the two metals are different.

5. The metal chelate of claim 4 wherein: said first metal in the form of an ion is selected from the group consisiting of $Fe^{2+}$, $Fe^{3+}$, $Co^{3+}$, $Mn^{2+}$, $Mn^{3+}$, $Cu^{2+}$, $Zn^{2+}$, $^{99m}Tc$, $^{111}In$, $^{52}Cu$ and $^{68}Ga$.

6. The metal chelate of claim 4 wherein: said second metal in the form of an ion is selected from the group consisting of $Gd^{3+}$, $Dy^{3+}$, $^{90}Y$, $^{212}Bi$, $^{225}Ac$, $^{99m}Tc$, $^{111}In$, $^{52}Cu$, $^{68}Ga$, and $^{188}Re$.

7. A compound of claim 1 having the formula

[complex macrocyclic structure with R₁, R₄, R₆, R₇, R₈, R₉, X₁, Y₁ and phenanthroline moiety]

or a pharmaceutically acceptable salt thereof, wherein $R_1$ is hydrogen, alkyl, arylalkyl, aryl, or $$-CH_2-\overset{\overset{O}{\|}}{C}-NR_2R_3$$

wherein $R_2$ and $R_3$ are independently hydrogen, alkyl, arylalkyl or aryl; or
$R_1$ is

[structures: —(CH₂)ₘ—phenyl(R₁₀,R₁₁) or —(CH₂)ₚ—CH(R₄)—X₁ or —(CH₂)ₘ—C(=O)—N(R₄)—A₁—phenyl(R₁₀,R₁₁)]

wherein $R_{10}$ and $R_{11}$ are each independently hydrogen, alkyl, —NO₂,

—NH$_2$,

—NH—C(=S)—NH—R$_4$, —NCS or —C(=O)—NR$_4$R$_{12}$;

R$_{12}$ is hydrogen, hydroxyalkyl, alkoxy, alkyl, aryl or arylalkyl;

A$_1$ is —(CH$_2$)$_q$-, —(CH=CH)—, —(CH=CH)$_2$- or a single bond; each —(CH$_2$)$_q$- is independently substituted with alkyl or hydroxyalkyl;

X$_1$ is —COOZ$_1$, PO$_3$(Z$_1$)$_2$ or —CONHOZ$_1$, —SO$_3$Z$_1$ where Z$_1$ is a hydrogen atom or a cation;

Y$_1$ is —OH, O-alkyl or —NHR$_1$;

R$_6$ and R$_7$ and R$_8$ and R$_9$ independently form together with the carbon atoms in the tetraazacyclododecane macrocycle to which they are attached, a fused fully or partially saturated nonaromatic cyclohexyl ring which is optionally unsubstituted or substituted by one or more halogen, alkyl, ether, hydroxy or hydroxyalkyl groups, and which is optionally further fused to a carboxylic ring, or R$_6$ and R$_7$ are each hydrogen and R$_8$ and R$_9$ form a fused fully or partially saturated non-aromatic cyclohexyl ring as defined above and R$_8$ and R$_9$ are hydrogen, or R$_6$, R$_7$ and R$_8$ are each hydrogen and R9 is R$_1$;

m is an integer from 0 to 3;

p is an integer from 0 to 3; and q is an integer from 1 to 5.

8. A compound of claim 1 having the formula or a pharmaceutically acceptable salt thereof, wherein R$_1$ is hydrogen, alkyl, arylalkyl, aryl, or

—CH$_2$—C(=O)—NR$_2$R$_3$ where R$_2$ and R$_3$ are independently hydrogen, alkyl, arylalkyl or aryl; or R$_1$ is or -continued —(CH$_2$)$_p$—CH(R$_4$)—X$_1$ where R$_4$ is hydrogen, alkyl, arylalkyl, aryl, alkoxy or hydroxyalkyl, or —(CH$_2$)$_m$—C(=O)—N(R$_4$)—A$_1$—(aryl with R$_{10}$, R$_{11}$)

where R$_{10}$ and R$_{11}$ are each independently hydrogen, alkyl, —NO$_2$,

—NH$_2$,

—NH—C(=S)—NH—R$_4$,

—NCS or

—C(=O)—NR$_4$R$_{12}$;

R$_4$ is hydrogen, alkyl, arylalkyl, aryl, alkoxy or hydroxyalkyl;

R$_{12}$ is hydrogen, hydroxyalkyl, alkoxy, alkyl, aryl or arylalkyl;

A$_1$ is —(CH$_2$)$_q$-, —(CH=CH)—, —(CH=CH)$_2$- or a single bond; each —(CH$_2$)$_q$- is independently substituted with alkyl or hydroxyalkyl;

X$_1$ is —COOZ$_1$, PO$_3$(Z$_1$)$_2$ or —CONHOZ$_1$, —SO$_3$Z$_1$ where Z$_1$ is a hydrogen atom or a cation;

R$_6$ and R$_7$ form together with the carbon atoms in the tetraazacyclododecane macrocycle to which they are attached, a fused fully or partially saturated nonaromatic cyclohexyl ring which is optionally unsubstituted or substituted by one or more halogen, alkyl, ether, hydroxy or hydroxyalkyl groups, and which is optionally further fused to a carboxylic ring, or R$_6$ and R$_7$ are each hydrogen or R$_6$, and R$_7$ form a fused or partially saturated non-aromatic cyclohexyl ring as defined above;

m is an integer from 0 to 3;

p is an integer from 0 to 3; and q is an integer from 1 to 5.

9. A compound of claim 1 having the formula or a pharmaceutically acceptable salt thereof, wherein Q$_3$ and Q$_4$ are each independently a ligand nucleus selected from the group consisting of 1,4,7,10-tetraazacyclododecane, 1,4,8,11-tetraazacyclo-tetradecane, ethylene-diamine, diethylenetriamine and triethylenetetramine substituted by at least one aminocarboxylate, aminophosphonate or aminohydroxamate chelating group; or $Q_3$ and $Q_4$ are independently a cyclic or non-cyclic linear or branched hydrocarbon optionally having one to six oxygen, sulfur or phosphorous atoms; and $R_{13}$ and $R_{14}$ are independently —CS— or —CO—.

10. A compound of claim 1 selected from the group consisting of:

2-[4-[(5R*,6R*-rac)-6-hydroxy-5,6-dihydro[1,10] phenanthrolin-5-yl]-7,10bis(2-hydroxy-2-oxoethyl)-1, 4,7,10-tetraazacyclododecan-1-yl]acetic acid;

(10aR*, 18bR*)-1,2,3,4,5,6,7,8,9,10,10a,18b-dodecahydro-[1,4,7,10]tetra-azacyclododecino [2,3-f] [1,10]-phenanthroline-1,4,7,10-tetraacetic acid;

4-[4-({[((5R*,6R-)-6-{[(4-{4-hydroxy-4-oxo-3[4,7,10-tris(carboxymethyl)-1,4,7,10-tetraazacyclododecan-1-yl]butyl}anilino)carbothioyl]]amino}-5,6-dihydro[1, 10]phenanthrolin-5yl)amino]carbothioyl]amino) phenyl]-2-[4,7,10-tris(carboxymethyl)-1,4,7,10-tetraazacyclododecan-1-yl]butanoic acid; and 4-(4-{[({2-[(3{-{[(4-{3-carboxy-3-[4,7,10-tris (carboxymethyl)-1,4,7,10-tetraazacyclodecan-1-yl] propyl}anilino)carbothioyl]amino}propanoyl)-(hydroxy)amino]ethyl}amino)carbothioyl] amino}phenyl)-2-[4,7,10-tris(carboxymethyl)-1,4,7, 10-tetraazacyclododecan-1-yl]butanoic acid.

11. A metal chelate comprising a compound of claim 10 and at least one metal ion of a metal of atomic number in the range 20–31, 38–50, 56–71 or 72–79.

12. A metal chelate comprising a compound of claim 10 and gadolinium.

13. A metal chelate comprising a compound of claim 10 and dysprosium.

14. A metal chelate comprising a compound of claim 10 associated with a transition metal ion selected from the group consisting of Fe(II), Fe(III), Co(III), Mn(II), Cu(II), Zn(II) and Ru(II).

15. A pharmaceutical composition comprising a metal chelate of claim 4 in a pharmaceutically acceptable vehicle.

16. A pharmaceutical composition comprising a metal chelate of claim 5 in a pharmaceutically acceptable vehicle.

17. A pharmaceutical composition comprising a metal chelate of claim 6 in a pharmaceutically acceptable vehicle.

18. A pharmaceutical composition comprising a metal chelate of claim 11 in a pharmaceutically acceptable vehicle.

19. A pharmaceutical composition comprising a metal chelate of claim 12 in a pharmaceutically acceptable vehicle.

20. A pharmaceutical composition comprising a metal chelate of claim 13 in a pharmaceutically acceptable vehicle.

21. A pharmaceutical composition comprising a metal chelate of claim 14 in a pharmaceutically acceptable vehicle.

22. A pharmaceutical composition for radiograhic imaging or radiotherapy in a kit form comprising a) a compound of claim 1;
b) a radioisotope complexed with said compound;
c) a pharmaceutically acceptable reducing agent; and
d) a buffering agent;
in a lyophilized form.

23. A method of diagnostic imaging comprising the steps of administering to a host a pharmaceutical composition of claim 15, and obtaining a diagnostic image of said host.

24. A method of therapy comprising the steps of administering to a host a pharmaceutical composition of claim 17, and monitoring the condition of said host.

25. A method of diagnostic imaging comprising the steps of administering to a host a pharmaceutical composition of claim 18, and obtaining a diagnostic image of said host.

26. The method of claim 23 wherein said image is a magnetic resonance, radiopharmaceutical or fluorescent image.

27. The method of claim 23 wherein said image is based on color change.

28. The method of claim 26 wherein said magnetic resonance, radiopharmaceutical and fluorescent images are recorded simultaneously.

29. The method of claim 23 wherein one metal ion in the chelate is a fluorescent metal ion or a metal ion forming a fluorescent species with the ligand and the other metal ion is a paramagnetic species.

30. The method of claim 23 wherein one metal ion in the chelate is a fluorescent metal ion or a metal ion forming a fluorescent species with the ligand and the other metal ion is a radionuclide.

31. A method of imaging comprising the steps of administering to a host a compound of claim 1, which compound is complexed with one or more metallic atoms suitable for obtaining a diagnostic image and one or more metal ions suitable for neutron capture therapy.

32. A process in which a solution of a heteropolymetallic complex is formed spontaneously in water comprising the steps of:

mixing an aqueous solution of a salt of a metal, said metal being selected from atoms having an atomic number of 21 to 31, 39 to 50 and 72 to 79 with an aqueous solution of a metal chelate, said metal chelate comprising a compound of formula

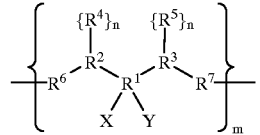

wherein

X—$R^1$—Y represent a first chelating group and $R^4$ and $R^5$ represent a second chelating group which is covalently linked to X—$R^1$—($R^2$13 $R^6$, $R^3$—$R^7$)—Y through $R^2$ and $R^3$, wherein X and Y are independently atoms which coordinate metal ions selected from the group consisting of N, O, S, and P;

$R^1$ is an aliphatic or an aromatic skeleton to which X and Y are covalently linked selected from the group consisting of straight-chain, branched, saturated and unsaturated hydrocarbons optionally substituted with oxygen, nitrogen, hydroxy or amino groups;

$R^2$ and $R^3$ are independently amino, oxy, mercapto, imino, hydrazido, ester, ketone, thiourea, aminoacetyl; or a saturated or unsaturated hydrocarbon substituted with amino, amido, oxy, mercapto, imino, hydrazido, ester, ketone, thiourea or aminoacetyl;

$R^4$ and $R^5$ are independently a ligand nucleus selected from the group consisting of a cyclic, non-cyclic linear and branched hydrocarbon having one to 6 nitrogen atoms, one of which at least is substituted by one carboxylate, phosphonate, oximate, diketonate, azino or hydroxamate group, said ligand nucleus optionally having one to six oxygen, sulfur or phosphorous atoms;

said $R^4$ and $R^5$ ligand nucleus forming a complex with a metal atom different from the metal atom formed with X—$R^1$—Y;

$R^6$ and $R^7$ are independently H, or straight-chain, branched, saturated or unsaturated hydrocarbons; or straight-chain, branched, saturated or unsaturated hydrocarbons substituted with amino, amide, ester, imino or hydrazido;

n is 1 to 35;

m is 1 to 10;

and another metal being selected from atoms having an atomic number of 21 to 31, 38 to 50 and 56 to 79; and adjusting the pH of the solution to 5 to 8 and/or gently heating the solution at about 40° to 85° C. to form the heteropolymetallic complex.

33. The process of claim 32 wherein X—$R^1$—Y together are

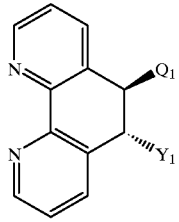

wherein $Y_1$ is —OH, O-alkyl, —SH, amide, NH-alkyl or NH-aryl;

$Q_1$ is a ligand nucleus covalently linked to the partially reduced phenanthroline ring and selected from the group consisting of 1.4,7,10-tetraazacyclododecane, 1,4,8,11-tetraazacyclo-tetradecane, ethylenediamine, diethylenetriamine and triethylenetetramine substituted by at least one amincarboxylate, aminophosphonate or aminohydroxamate; and $R_1$ is hydrogen, alkyl, arylalkyl, aryl, or

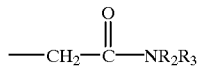

wherein $R_2$ and $R_3$ are independently hydrogen, alkyl, arylalkyl or aryl;

$R_1$ is

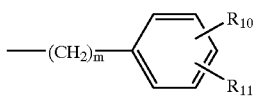

or

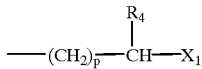

wherein $R_4$ is hydrogen, alkyl, arylalkyl, aryl, alkoxy or hydroxyalkyl;

or

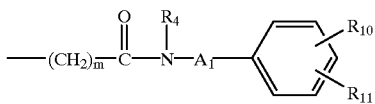

wherein $R_{10}$ and $R_{11}$ are each independently hydrogen, alkyl, —$NO_2$,

—$NH_2$,

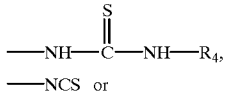

—NCS or

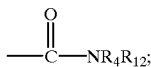

$R_{12}$ is hydrogen, hydroxyalkyl, alkoxy, alkyl, aryl or arylalkyl;

$A_1$ is —$(CH_2)_q$-, —(CH=CH)—, —$(CH=CH)_2$- or a single bond; each —$(CH_2)_q$- is independently substituted with alkyl or hydroxyalkyl;

$X_1$ is —$COOZ_1$, $PO_3(Z_1)_2$ or —$CONHOZ_1$, —$SO_3Z_1$ where $Z_1$ is a hydrogen atom or a cation;

m is an integer from 0 to 3;

p is an integer from 0 to 3; and q is an integer from 1 to 5.

* * * * *